United States Patent
Edwards et al.

(10) Patent No.: US 6,869,590 B2
(45) Date of Patent: Mar. 22, 2005

(54) LABELED MACROPHAGE SCAVENGER RECEPTOR ANTAGONISTS FOR IMAGING ATHEROSCLEROSIS AND VULNERABLE PLAQUE

(75) Inventors: David Scott Edwards, Burlington, MA (US); Shuang Liu, Chelmsford, MA (US)

(73) Assignee: Bristol-Myers Squibb Pharma Company, Princeton, NJ (US)

( * ) Notice: Subject to any disclaimer, the term of this patent is extended or adjusted under 35 U.S.C. 154(b) by 0 days.

(21) Appl. No.: 10/080,974

(22) Filed: Feb. 22, 2002

(65) Prior Publication Data

US 2002/0127181 A1 Sep. 12, 2002

Related U.S. Application Data

(60) Provisional application No. 60/270,954, filed on Feb. 23, 2001.

(51) Int. Cl.$^7$ .......................... A61K 51/00; A61M 36/14
(52) U.S. Cl. .......................... 424/1.65; 534/14; 534/10; 424/1.11
(58) Field of Search ............................. 424/1.11, 1.65, 424/9.1, 9.3, 9.4, 9.5, 9.6, 9.7, 9.8; 534/7, 10–16, 223, 569; 206/570

(56) References Cited

U.S. PATENT DOCUMENTS

| | | | |
|---|---|---|---|
| 4,577,042 A | * | 3/1986 | Collins et al. ............... 564/158 |
| 4,678,667 A | | 7/1987 | Meares et al. ................ 424/85 |
| 4,752,141 A | | 6/1988 | Sun et al. .................... 374/161 |
| 4,885,363 A | | 12/1989 | Tweedle et al. ............. 540/465 |
| 4,923,985 A | | 5/1990 | Gansow et al. ............. 540/474 |
| 4,986,671 A | | 1/1991 | Sun et al. .................... 374/131 |
| 5,053,053 A | | 10/1991 | De Labbey et al. ............. 8/423 |
| 5,087,440 A | | 2/1992 | Cacheris et al. ............... 424/9 |
| 5,155,215 A | | 10/1992 | Ranney ........................ 534/16 |
| 5,275,594 A | | 1/1994 | Baker et al. .................. 606/12 |
| 5,310,535 A | | 5/1994 | Kruper, Jr. et al. ......... 424/1.53 |
| 5,428,154 A | | 6/1995 | Gansow et al. ............. 540/465 |
| 5,428,156 A | | 6/1995 | Mease et al. ................ 540/474 |
| 5,739,323 A | | 4/1998 | Kruper, Jr. et al. ......... 540/474 |
| 5,744,120 A | | 4/1998 | Edwards et al. ............ 424/1.64 |
| 5,756,065 A | | 5/1998 | Wilson et al. .............. 424/1.53 |
| 5,846,519 A | | 12/1998 | Tweedle et al. ......... 424/9.363 |
| 5,879,659 A | | 3/1999 | Edwards et al. ............ 424/1.69 |
| 5,958,374 A | | 9/1999 | Meares et al. .............. 525/1.65 |
| 6,010,679 A | | 1/2000 | Edwards et al. ............ 424/1.69 |

FOREIGN PATENT DOCUMENTS

| | | |
|---|---|---|
| AU | 35519/93 | 9/1993 |
| EP | 0 292 689 A2 | 11/1988 |
| EP | 0 382 583 B1 | 8/1990 |
| EP | 0 565 930 A1 | 10/1993 |
| WO | WO 87/05030 | 8/1987 |
| WO | WO 89/01476 | 2/1989 |
| WO | WO 90/12050 | 10/1990 |
| WO | WO 91/14458 | 10/1991 |
| WO | WO 93/06868 | 4/1993 |
| WO | WO 95/26206 | 10/1995 |
| WO | WO 97/32862 | 9/1997 |
| WO | WO 98/11475 | 3/1998 |
| WO | WO 98/53858 | 12/1998 |
| WO | WO 99/07382 | 2/1999 |
| WO | WO 99/67284 | 12/1999 |
| WO | WO 00/03704 | 1/2000 |
| WO | WO 00/06147 | 2/2000 |

OTHER PUBLICATIONS

Agatston, A.S., et al., "Quantification of coronary artery calcium using ultrafast computed tomography," *J. Am. Coll. Cardiol.*, Mar. 15, 1990, 15(4), 827–832.

Alderman, E.L., et al., "Five–year angiographic follow–up of factors associated with progression of coronary artery disease in the coronary artery surgery study," *J. Am. Coll. Cardiol.*, Oct. 1993, 22(4), 1141–1154.

Ambrose, J.A., et al., "Angiographic progression of coronary artery disease and the development of myocardial infarction," *J. Am. Coll. Cardiol.*, Jul. 1988, 12(1). 56–62.

Ambrose, J.A., "Angiographic correlations of advanced coronary lesions in acute coronary syndromes," Syndromes of Atherosclerosis: Correlations of Clinical Imaging and Pathology, V. Fuster, V. (Ed.), *Futura Publishing Co., Inc.*, 1996, 105–122.

Baumgartner, H.–R., Eine neue methode zur erzeugung von thrombin durch gezielte Überdehnung der gefaβwand, *Gesamte Exp. Med.*, 1963, 137, 227–247 (Summary in English on p. 243).

Becker, C.R., et al., "Visualization and quantification of coronary calcifications with electron beam and spiral computed tomography," *Eur. Radiol.*, 2000, 10, 629–635.

Bhorade, R., et al., "Macrocyclic chelators with paramagnetic cations are internalized into mammalian cells via a HIV–Tat dervied membrane translocation peptide," *Bioconjugate Chem.*, May/Jun. 2000, 11(3), 301–305.

Brechbiel, M.W., et al., "Backbone–substituted DTPA ligands for $^{90}Y$ radioimmunotherapy," *Bioconjugate Chem.*, 1991, 2, 187–194.

Brechbiel, M.W., et al., "Synthesis of 1–(p–isothiocyanato-benzyl) derivatives of DTPA and EDTA. Antibody labeling and tumor–imaging studies," *Inorg. Chem.*, 1986, 25, 2772–2781.

(List continued on next page.)

*Primary Examiner*—Dameron L. Jones
(74) *Attorney, Agent, or Firm*—Warren K. Volles; Woodcock Washburn LLP

(57) ABSTRACT

Detectably labeled macrophage scavenger receptor antagonists useful for the diagnosis and monitoring of various cardiovascular diseases including but not limited to atherosclerosis, vulnerable plaque, coronary artery disease, renal disease, thrombosis, transient ischemia due to clotting, stroke, myocardial infarction, organ transplant, organ failure and hypercholesterolemia.

49 Claims, No Drawings

OTHER PUBLICATIONS

Brundage, B.H., et al., "the calcium story and electron beam computed tomography," Syndromes of Atherosclerosis: Correlations of Clinical Imaging and Pathology, V. Fuster, V. (Ed.), *Futura Publishing Co., Inc.*, 1996, 417–427.

Budoff, M.J., et al., "Rates of progression of coronary calcium by electron beam tomography," *Am. J. Cardiol.*, Jul. 1, 2000, 86, 8–11.

Carrington, C., could coronary calcium screening prevent this? *Diagnostic Imaging*, Apr. 2000, 48–53.

Delbeke, D., "Oncological applications of FDG PET imaging," *J. Nucl. Med.*, Oct. 1999, 40(10), 1706–1715.

Dinsmore, R.E., et al., "Imaging techniques in carotid and peripheral vascular disease," Syndromes of Atherosclerosis: Correlations of Clinical Imaging and Pathology, V. Fuster (Ed.), *Futura Publishing Co., Inc.*, 1996, 277–289.

Doherty, T.M., et al., "Coronary calcium: the good, the bad, and the uncertain," *Am. Heart J.*, May 1999, 137(5), 806–814.

Doyle, M., et al., "Magnetic resonance coronary artery imaging," Syndromes of Atherosclerosis: Correlations of Clinical Imaging and Pathology, V. Fuster (Ed.), *Futura Publishing Co., Inc.*, 1996, 313–332.

Elmaleh, D.R., et al., "Rapid noninvasivedetection of experimental atherosclerotic lesions with novel $^{99m}$Tc–labeled diadenosine tetraphosphates," *Proc. Natl. Acad. Sci. USA*, Jan. 1998, 95, 691–695.

Erbel, R., et al., "Electron–beam computed tomography for detection of early signs of coronary arteriosclerosis," *Eur. Heart J.*, 2000, 21, 720–732.

Farb, A., et al., "Sudden coronary death," *Circulation*, Oct. 1, 1995, 92(7), 1701–1709.

Fuster, V., et al., "The pathogenesis of coronary artery disease and the acute coronary syndromes," *N. Engl. J. Med.*, Jan. 23, 1992, 326(4), 242–250.

Galis, Z.S., et al., "Macrophage foam cells from experimental atheroma constitutively prduce matrix–degrading proteinases," *Proc. Acad. Sci. USA*, Jan. 1995, 92, 402–406.

Glover, G.H., et al., "Research directions in MR imaging," *Radiology*, May 1998, 207(2), 289–295.

Goldstein, J.L., et al., "Receptor–mediated endocytosis of low–density lipoprotein in cultered cells," *Methods Enzymol.*, 1983, 98, 241–261.

Goldstein, J.L., et al., "Binding site on macrophages that mediates uptake and degradation of acetylated low density lipoprotein, producing massive cholesterol deposition," *Proc. Natl. Acad. Sci. USA*, Jan. 1979, 76(1), 333–337.

Goyen, M., et al., "MR–angiography: the role of contrast agents," *Eur. J. Radiol.*, 2000, 34, 247–256.

Grist, T.M., et al., "Nuclear magnetic resonance imaging as applied to carotid and peripheral atherosclerotic vascular disease," Syndromes of Atherosclerosis: Correlations of Clinical Imaging and Pathology, V. Fuster (Ed.), *Futura Publishing Co., Inc.*, 1996, 333–362.

Janowitz, W.R., et al., "Differences in prevalence and extent of coronary artery calcium detected by ultrafast computed tomography in asymptomatic men and women," *Am. J. Cardiol.*, Aug. 1, 1993, 72(3), 247–254.

Kaski, J.C., et al., "Rapid angiographic progression of coronary artery disease in patients with angina pectoris," *Circulation*, Oct. 15, 1995, 92(8), 2058–2065.

Knopp, M.V., et al., "Contrast agents for MRA: future directions," *J. Magn. Reson. Imaging*, 1999, 10, 314–316.

Kohler, T.R., "Imaging of carotid artery lesions: a surgeon's view," Syndromes of Atherosclerosis: Correlations of Clinical Imaging and Pathology, V. Fuster (Ed.), *Futura Publishing Co., Inc.*, 1996, 205–223.

Ku, D.N., et al., "Pulsatile flow and atherosclerosis in the human carotid bifurcation," *Atheriosclerosis*, May/Jun. 1985, 5(3), 293–302.

Lewin, M., et al., "Tat peptide–derivatized magnetic nanoparticles allow in vivo tracking and recovery of progenitor cells," *Nat. Biotechnol.*, Apr. 2000, 18, 410–414.

Lin, Y.–Z., et al., "Inhibition of nuclear translocation of transcription factor NF–←–B by a synthetic peptide containing a cell membrane–permeable motif and nuclear localization sequence," *J. Biol. Chem.*, Jun. 16, 1995, 270(24), 14255–14258.

Little, W.C., et al., "Can coronary angiography predict the site of a subsequent myocardial infarction in patients with mild–to–moderate coronary artery disease?," *Circulation*, 1988, 78, 1157–1166.

Marmion, M., et al., "Tracers and contrast agents in cardiovascular imaging: present and future," *J. Nucl. Biol. Med.*, 1996, 40, 121–131.

Mazzone, A., et al., "Increased expression of neutrophil and monocyte adhesion molecules in unstable coronary artery disease," *Circulation*, 1993, 88, 358–363.

McVeigh, E.R., "MRI of myocardial function: motion tracking techniques," *Magn. Reson. Imaging*, 1996, 14(2), 137–150.

Meaney, J.F.M., , et al., "Pulmonary magnetic resonance angiography," *J. Magn. Reson. Imaging*, 1999, 10, 326–338.

Moi, M.K., et al., "The peptide way to macrocyclic bifunctional chelating agents: synthesis of 2–(p–nitrobenzyl)–1,4,7,10–tetraazacyclododecane–N,N',N'', N'''–tetraacetic acid and study of its yttrium(III) complex," *J. Am. Chem. Soc.*, 1988, 110, 6266–6267.

Moi, M.K., et al., "Copper chelates as probes of biological systems: stable copper complexes with a macrocyclic bifunctional chelating agent," *Anal. Biochem.*, 1985, 148, 249–253.

Morris, M.C., et al., "A new peptide vector for efficient delivery of oligonucleotides into mammalian cells," *Nucleic Acids Res.*, 1997, 25(14), 2730–2736.

Narula, J., et al., "Noninvasive localization of experimental atherosclerotic lesions with mouse/human chimeric Z2D3 F(ab')$_2$ specific for the proliferating smooth muscle cells of human atheroma," *Circulation*, 1995, 92, 474–484.

Narula, J., et al., "Gamma imaging of atherosclerotic lesions: the role of antibody affinity in in vivo target localization," *J. Nucl. Cardiol.*, 1996, 3, 231–241.

Narula, J., "Strategic targeting of antherosclerotic lesions," *J. Nucl. Cardiol.*, 1999, 6, 81–90.

Narula, J., "POPE': predicting outcome by plaque evaluation," *J. Nucl. Med. Commun.*, 2000, 21, 601–608.

Orford, J.L., et al., "The comparative pathobiology of atherosclerosis and restenosis," *Am. J. Cardiol.*, 2000, 86 (suppl.), 6H–11H.

Patel, M.R., et al., "Preoperative assessment of the carotid bifurcation," *Stroke*, 1995, 26, 1753–1758.

Polak, J.F., "Focus on imaging at the American heart association annual meeting," *Radiology*, Aug. 2000, 216, 323–324.

Remington's Pharmaceutical Sciences, 17$^{th}$ Ed., *Mack Publishing Co., Easton, PA*, 1985, p. 1418.

Rumberger, J.A., "Electron beam CT and coronary calcium score," *Circulation*, 1998, 97, 2095–2097.

Runge, V.M., "Safety of approved MR contrast media for intravenous injection," *J. of Magn. Reson. Imaging*, 2000, 12, 205–213.

Schmermund, A., et al., "Usefulness of topography of coronary calcium by electron–beam computed tomography in predicting the natural history of coronary atherosclerosis," *Am. J. Cardiol.*, 2000, 86, 127–132.

Tunstall–Pedoe, H., et al., Who–Monica Project, "Myocardial infarction and coronary deaths in the world health organization MONICA Project," *Circulation*, 1994, 90, 583–612.

Vaidyanathan, G., et al., "Labeling proteins with fluorine–18 using N–succinimidyl 4–[$^{18}$F]fluorobenzoate," *Nucl. Med. Biol.*, 1992, 19(3), 275–281.

Vallabhajosula, S., et al., "Atherosclerosis: imaging techniques and the evolving role of nuclear medicine," *J. Nucl. Med.*, 1997, 38, 1788–1796.

Weissleder, R., et al., "Drug targeting in magnetic resonance imaging," *Magnetic Resonance Quarterly*, 1992, 8(1), 55–63.

Welch, M.J., et al., "The potential role of generator–produced radiopharmaceuticals in clinical PET," *J. Nucl. Med.*, 2000, 41, 315–317.

Wexler, L., et al., "Coronary artery calcification: pathophysiology, epidemiology, imaging methods, and clinical implications," *Circulation*, 1996, 94, 1175–1192.

Anderson, C.J., et al., "Radiometal–labeled agents (non–technetium for diagnostic imaging," *Chem. Rev.*, 1999, 99(9), 2219–2234.

Anson, F.C., et al., "Interconversion of planar and nonplanar N–amido ligands. Thermodynamically stable nonplanar N–anudi kugabdsm" *J. Am. Chem. Soc.*, 1996, 108(21), 6593–6605.

Antopolsky, M., et al., "Peptide–oligonucleotide phosphorothioate conjugates with membrane translocation and nuclear localization properties," *Bioconjugate Chem.*, 1999, 10, 598–606.

Atsma, D.E., et al., "Potential of $^{99m}$Tc–LDLs labeled by two different methods for scintigraphic detection of experimental atherosclerosis in rabbits," *Arteroscler and Thromb*, Jan. 1993, 13(1), 78–83.

Barrington, S.F., "Clinical use of PET in neurology," *Nucl. Med. Commun.*, Mar. 2000, 21(3), 237–240.

Bar–Shalom, R., et al., "PET imaging in oncology," *Seminars in Nucl. Med.*, Jul. 2000, 30(3), 150–185.

Bayley, H., "Protein therapy –delivery guaranteed," *Nat. Biotechnol.*, Nov. 1999, 17(11), 1066–1067.

Bousquet, J.–C., et al., "Characterization of a new paramagnetic complex$^1$," *Radiology*, Mar. 1988, 166(3), 693–698.

Caravan, P., et al., "Gadolinium(III) chelates as MRI contract agents: structure, dynamics, and applications," *Am. Chem. Soc.*, 1999, 99(9), 2293–2352.

Cerqueira, M.D., et al., "Current status of radionuclide tracer imaging of thrombi and atheroma," *Seminars in Nucl. Med., W.B. Saunders Co.,*, Oct. 1999, 29(4), 339–351.

Duncan, K., "Radiopharmaceuticals in PET imaging," *J. of Nucl. Med. Technol.*, 1998, 26, 228–234.

Fawell, S., et al., "Tat–mediated delivery of heterologous proteins into cell," *Proc. Natl. Acad. Sci. USA*, Jan. 1994, 91, 664–668.

Freeman, M., et al., "Expression of type I and type II bovine scavenger receptors in Chinese hamster ovary cells: Lipid droplet accumulation and nonreciprocal cross competition by acetylated and oxidized low density lipoprotein," *Proc. Natl. Sci. USA*, Jun. 1991, 88, 4931–4935.

Haynes, N.G., et al., "Performance of a $^{62}$Zn/$^{62}$Cu generator in clinical trials of PET perfusion agent $^{62}$Cu–PTSM," *J. Nucl. Med.*, 2000, 41, 309–314.

Hnatowich, D.J., et al., "Radioactive labeling of antibody: a simple and efficient method," *Science*, 1983, 220, 613–616.

Iuliano, L., et al., "Preparation and biodistribution of $^{99m}$technetium labeled oxidized LDL in man," *Atherosclerosis*, Aug. 1996, 126(1), 131–141.

Josephson, L., et al., "High–efficiency intracellular magnetic labeling with novel superparamagnetic–tat peptide conjugates," *Bioconjugate Chem.*, 1999, 10, 186–191.

Jurisson, S.S., et al., "Potential technetium small molecule radiopharmaceuticals," *Chem. Rev.*, 1999, 99, 2205–2218.

Krejcarek, G.E., et al., "Covalent attachment of chelating groups to macromolecules," *Biochem & Biophys. Res. Commun.*, 1977, 77(2), 581–585.

Lees, A.M., et al., "Imaging human atherosclerosis with $^{99m}$Tc–labeled low density lipoproteins," *Arteriosclerosis*, Sep./Oct. 1988, 8, 461–470.

Lindgren, M., et al., "Cell–penetrating peptides," *TiPS*, Mar. 2000, 21, 99–103.

Liu S., et al., "Bifunctional chelators for therapeutic lanthanide radiopharmaceuticals," *Bioconjugate Chemistry*, 2001, 12, 7–34.

Liu, S., et al., "$^{99m}$Tc labeling of highly potent small peptides," *Bioconjugate Chem.*, 1997, 8, 621–636.

Liu, S., et al., "$^{99m}$Tc–labeled small peptides as diagnostic radiopharmaceuticals," *Chem. Rev.*, 1999, 99, 2235–2268.

Lysko, P.G., et al., "Identification of a small–molecule, nonpeptide macrophage scavenger receptor antagonist," *J. Pharmacol. Exp. Ther.*, Jun. 1999, 289(3), 1277–1285.

Maisley, M.N., "Clinical PET in cardiology and cardiac surgery," *Nucl. Med. Commun.*, 2000, 21, 234–236.

Margerstadt, M., et al., "Gd(DOTA): an alternative to Gd(DTPA) as a $T_{1,2}$ relaxation agent for NMR imaging or spectroscopy," *Magn. Reson. Med.*, 1986, 3, 808–812.

Meares, C.F., et al., "Chelating agents for the binding of metal ions to antibodies," *Nucl. Med. Biol.*, 1986, 13(4), 311–318.

Nunan, T.O., et al., "PET in oncology II –other tumours," *Nucl. Med. Commun.*, 2000, 21, 229–233.

O'Doherty, M.J., "PET in oncology I –lung, breast, soft tissue sarcoma," *Nucl. Med. Commun.*, 2000, 21, 224–229.

Phelps, M.E., "PET: the merging of biology and imaging into molecular imaging," *J. Nucl. Med.*, 2000, 41, 661–681.

Pooga, M., "Cell penetrating PNA constructs regulate galanin receptor levels and modify pain transmission in vivo," *Nat. Biotechnol.*, Sep. 1998, 16, 857–861.

Ross, R., "The pathogenesis of atherosclerosis: a perspective for the 1990s," *Nature*, Apr. 29, 1993, 362, 801–809.

Runge, V.M., et al., *Radiology*, 1988, 166, 835–838.

Schluesener, H.J., "Protection against experimental nervous systems autoimmune disease by a human immunodeficiency virus–1 Tat peptide–based polyvalent vaccine," *J. of Neurosci. Res.*, 1996, 46(2), 258–262 (abstract).

Schwartz, J.J., et al., "Peptide–mediated cellular delivery," *Current Opinions in Molecular Therapeutics*, 2000, 2(2), 162–167.

Singh, D., et al., "Peptide–based intracellular shuttle able to facilitate gene transfer in mammalian cells," *Bioconjugate Chem.*, 1999, 10, 745–754.

Stern, W., et al., "Dynamic MR imaging of liver metastases with GD–EOB–DTPA," *Acta Radiologica*, 2000, 41, 255–262.

Sutcliffe–Goulden, J.L., et al., "Solid phase synthesis of [$^{18}$F]labeled peptides for positron emission tomography," *Bioorg. & Med. Chem. Lett.*, Jul. 2000, 10(14), 1501–1503.

Toussaint, J.-F., et al., "$T_2$–weighted contrast for NMR characterization of human atherosclerosis," *Arterioscler. Thromb Vasc Biol.*, 1995, 15, 1533–1542.

Toussaint, J.-F., et al., "Magnetic resonance images lipid, fibrous, calcified, hemorrhagic, and thrombotic components of human atherosclerosis in vivo," *Circulation*, 1996, 94, 932–938.

Vaidyanathan, G., et al., "Protein radiohalogenation: observations on the design of N–succinimidyl ester acylation agents," *Bioconjugate Chem.*, 1990, 1, 269–273.

Vaidyanathan, G., et al., "Improved synthesis of N–succinimidyl 4–[$^{18}$F]fluorobenzoate and its application to the labeling of monoclonal antibody fragment," *Bioconjugate Chem.*, 1994, 5, 352–356.

Vaidyanathan, G., et al., "Fluorine–18 labeled chemotactic peptides: a potential approach for the PET imaging of bacterial infection," *Nucl. Med. Biol.*, 1995, 22(6), 759–764.

Virgolini, I., et al., "Autologous low–density lipoprotein labeling allows charcaterization of human atherosclerotic lesions in vivo as to presence of foam cells and endothelial coverage," *Eur. J. of Nucl. Med.*, 1991, 18, 948–951.

Volkert, W.A., et al., "Therapeutic radiopharmaceuticals," *Chem. Rev.*, 1999, 99, 2269–2292.

Yuan, C., et al., "Techniques for high–resolution MR imaging of atherosclerotic plaque," *J. of Magn. Reson. Imaging*, 1994, 4, 43–49.

\* cited by examiner

LABELED MACROPHAGE SCAVENGER RECEPTOR ANTAGONISTS FOR IMAGING ATHEROSCLEROSIS AND VULNERABLE PLAQUE

REFERENCE TO RELATED APPLICATIONS

This application claims priority to U.S. provisional application 60/270,954, filed Feb. 23, 2001, incorporated herein by reference in its entirety.

FIELD OF THE INVENTION

This invention provides detectably labeled macrophage scavenger receptor antagonists useful for the diagnosis and monitoring of various cardiovascular diseases including but not limited to atherosclerosis, vulnerable plaque, coronary artery disease, renal disease, thrombosis, transient ischemia due to clotting, stroke, myocardial infarction, organ transplant, organ failure and hypercholesterolemia. The macrophage receptor antagonists are biomolecules that bind to the macrophage scavenger receptor class A (SR-A), which are over-expressed in atherosclerotic lesions. The detectable labels include radionuclides for nuclear scintigraphy or positron emission tomography (PET), paramagnetic metal ions or superparamagnetic particles for magnetic resonance imaging (MRI), heavy metal ions for X-ray or computed tomography (CT), gas-filled microbubbles for targeted ultrasonography (US), or optical dyes for optical imaging, porphyrins or texaphyrins for NMR, fluoresent imaging or photodynamic therapy. This invention also provides in vivo methods for detection and imaging of those vascular pathologies by administering to a patient a detectably labeled scavenger receptor antagonist of the present invention and detecting or imaging the location of the pathologies. This invention also provides pharmaceutically acceptable compositions comprising the detectably labeled scavenger receptor antagonists of the present invention.

BACKGROUND OF THE INVENTION

Cardiovascular diseases are the leading cause of death in the U.S., accounting annually for more than one million deaths. Atherosclerosis is the major contributor to coronary heart disease and a primary cause of non-accidental death in Western countries (Coopers, E. S. *Circulation* 1993, 24, 629–632; WHO-MONICA Project. *Circulation* 1994, 90, 583–612). Considerable effort has been made in defining the etiology and potential treatment of atherosclerosis and its consequences, including myocardial infarction, angina, organ failure and stroke. Despite this effort, there are many unanswered questions including how and when atherosclerotic lesions become vulnerable and life-threatening, the best point of intervention, and how to detect and monitor the progression of lesions.

It is well-documented that multiple risk factors contribute to atherosclerosis. Such risk factors include, e.g., hypertension, elevated total serum cholesterol, high levels of low density lipoprotein (LDL) cholesterol, low levels of high density lipoprotein (HDL) cholesterol, diabetes mellitus, severe obesity, and cigarette smoking (Orford et al. *Am. J. Cardiol.* 2000, 86 (suppl.) 6H–11H). To date, treatment of atherosclerosis has been focussed on lowering cholesterol levels and modifying lipids. However, recent studies have indicated that 40% of deaths due to coronary disease occurred in men with total cholesterol levels of below 220 mg/dl. (Orford et al. *Am. J. Cardiol.* 2000, 86 (suppl.) 6H–11H).

In atherogenesis, elevated plasma levels of LDL lead to the chronic presence of LDL in the arterial wall. The modified LDL activates endothelial cells, which attract circulating monocytes (Orford et al. *Am. J. Cardiol.* 2000, 86 (suppl.) 6H–11H). These monocytes enter the vessel wall, differentiate into macrophages, and subject the modified lipoproteins to endocytosis through scavenger receptor pathways. This unrestricted uptake eventually leads to the formation of lipid-filled foam cells, the initial step in atherosclerosis. If the macrophage is present in an environment that is continually generating modified LDL, it will accumulate lipid droplets of cholesteryl esters, continuing until the macrophage dies from its toxic lipid burden. The released lipid then forms the acellular necrotic core of the atherosclerotic lesion. Subsequent recruitment of fibroblasts, vascular smooth muscle cells, circulating monocytes, and T-lymphocytes complete the inflammatory response and the formation of the mature atherosclerotic plaque. Macrophage-derived foam cells are concentrated in the shoulders of plaques, where their secreted proteinases and collagenases may contribute to plaque rupture, which may lead to a fatal thrombotic event.

The progression of coronary atherosclerotic disease can be divided into five phases (Fuster et al. *N. Engl. J. Med.* 1992, 326, 242–250). Phase 1 is represented by a small plaque that is present in most people under the age of 30 years regardless of their country of origin. Phase 1 usually progresses slowly (types I to III lesions). Phase 2 is represented by a plaque, not necessarily very stenotic, with a high lipid content that is prone to rupture (types IV and Va lesions). The plaque of phase 2 may rupture with a predisposition to change its geometry and to the formation of mural thrombus. These processes, by definition, represent phase 3 (type I lesion), with a subsequent increase in stenosis, possibly resulting in angina or ischemic sudden death. The mural and occlusive thrombi from plaques of phases 3 and 4, by being organized by connective tissue, may contribute to the progression of the atherosclerotic process represented by severely stenotic or occlusive plaques of phase 5 (type Vb and Vc lesions). The severely stenotic plaques of phase 5, by a phenomenon of stasis and/or deendothelialization, can become complicated by a thrombus and/or myopreliferative response, also leading to an occlusive plaque of phase 5. Two-thirds of coronary occlusions are the result of this late stenotic type of plaques and are unrelated to plaque rupture. Unlike the rupture of less-stenotic lipid-rich plaques which leading to occlusion and subsequent infarction or other acute coronary syndromes, this process of occlusion from late stenotic plaques tends to be silent because the proceeding severe stenosis and ischemia enhance protective collateral circulation (Fuster et al, *N. Engl. J. Med.,* 1992, 326, 242–250).

The ability to detect, quantitate, and monitor atherosclerotic plaque formation is of major clinical importance owing to the progression of these plaques to stable coronary artery disease or to the occurrence of acute ischemic syndromes caused by the rupture of vulnerable plaque. Various imaging modalities for the detection of atherosclerotic lesion and thrombosis associated with plaque rupture have been reviewed (Vallabhajosula, S. and Fuster, V. *J. Nucl. Med.* 1997, 38, 1788–1796; Marmion, M. and Deutsch, E. *J. Nucl. Biol. Med.* 1996, 40, 121–131; Cerqueira, M. D. *Seminars Nucl. Med.* 1999, 29, 339–351; Narula, J. *J. Nucl. Cardiol.* 1999, 6, 81–90; Narula, J. *Nucl. Med. Commun.* 2000, 21, 601–608; Meaney et al. *J. Magn. Reson. Imaging* 1999, 10, 326–338; Knopp et al. *J. Magn. Reson. Imaging* 1999, 10, 314–316; Goyen et al. *Eur. J. Radiol.* 2000, 34, 247–256; Becker et al. *Eur. Radiol.* 2000, 10, 629–635).

Several invasive and noninvasive techniques are routinely used to image atherosclerosis and to assess the progression and stabilization of the disease. These include coronary angiography, intravascular ultrasound angioscopy, intravascular magnetic resonance imaging, and thermal imaging of plaque using infrared catheters. These techniques have been successfully used to identify vulnerable plaques. However, these techniques are generally invasive.

Soluble markers, such as P-selectin, von Willebrand factor, Angiotensin-converting enzyme (C146), C-reactive protein, D-dimer (Ikeda et al. *Am. J. Cardiol.,* 1990, 65, 1693–1696.), and activated circulating inflammatory cells are found in patients with unstable angina pectoris, but it is not yet known whether these substances predict infarction or death (Mazzone et al. *Circulation,* 1993, 88, 358–363.). It is known, however, that the presence of these substances cannot be used to locate the involved lesion.

Temperature sensing elements contained in catheters have been used for localizing plaque on the theory that inflammatory processes and cell proliferation are exothermic processes. For example, U.S. Pat. No. 4,986,671 discloses a fiber optical probe with a single sensor formed by an elastic lens coated with light reflective and temperature dependent material over which is coated a layer of material that is absorptive of infrared radiation. Such devices are used to determine characteristics of heat or heat transfer within a blood vessel. The devices measure such parameters as the pressure, flow and temperature of the blood in a blood vessel. U.S. Pat. No. 4,752,141 discloses a fiberoptic device for sensing temperature of the arterial wall upon contact. However, discrimination of temperature by contact requires knowing where the catheter is to be placed. These techniques using catheters or devices are invasive, and sometimes may result in or trigger plaque formation or rupture.

An angiogram simply reflects luminal diameter and provides a measure of stenosis with excellent resolution. An angiogram, however, does not image the vessel wall or the various histopathological components. Nevertheless, this technique has become the mainstay of the diagnosis of coronary, carotid, and peripheral artery lesions (Galis et al, *Proc. Acad. Sci. USA,* 1995, 92, 402–406; Ambrose, J. A. In: Fuster, V. (Ed.). *Syndromes of Atherosclerosis: correlations of clinical imaging and pathology.* Armonk, N.Y.: Futura Publishing Company, Inc., 1996, 105–122; Kohler, T. R. In: Fuster, V. (Ed.). *Syndromes of Atherosclerosis: correlations of clinical imaging and pathology.* Armonk, N.Y.: Futura Publishing Company, Inc., 1996, 205–223; Dinsmore, R. E. and Rivitz, S. M. In: Fuster, V. (Ed.). *Syndromes of Atherosclerosis: correlations of clinical imaging and pathology.* Armonk, N.Y.: Futura Publishing Company, Inc., 1996, 277–289), and is the "gold standard" for anatomic diagnosis despite limited specificity and sensitivity.

An angiogram may be useful for predicting a vulnerable plaque, since low-shear regions opposite flow dividers are more likely to develop atherosclerosis (Ku et al. *Atherosclerosis* 1985, 5, 292–302). However, most patients who develop acute myocardial infarction or sudden death have not had prior symptoms, much less an angiography (Farb et al. *Circulation* 1995, 93, 1701–1709). Certain angiographic data have revealed that a regular plaque profile is a fairly specific, though insensitive, indicator of thrombosis (Kaski et al. *Circulation* 1995, 92, 2058–2065). Such plaques are likely to progress to complete occlusion, while others are equally likely to progress, but less often reach the point of complete occlusion (Aldeman et al. *J. Am. Coll. Cardiol.* 1993, 22, 1141–1154). Those that do abruptly progress to occlusion actually account for most myocardial infarctions (Ambrose et al. *J. Am. Coll. Cardiol.* 1988, 12, 56–62; Little et al. *Circulation* 1988, 78, 1157–1166). One of the major limitations of angiography is that diffuse atherosclerotic disease may narrow the entire lumen of the artery, and as a result, angiography underestimates the degree of stenosis.

The size of the plaque occlusion is not necessarily determinative. Studies show that most occlusive thrombi are found over a ruptured or ulcerated plaque that is estimated to have produced a stenosis of less than 50% of the vessel diameter. Such stenoses are not likely to cause angina or result in a positive treadmill test. In fact, most patients who die of myocardial infarction do not have three-vessel disease or severe left ventricular dysfunction (Farb et al. *Circulation* 1995, 93, 1701–1709).

Angioscopy is another technique for the visualization of artery walls, rather than the lumen, and for the characterization of atherosclerotic disease. The angioscopy technique reveals the plaque and surface features not seen by angiography. In addition, it allows the observation of the color (red, white or yellow) of the material in the artery, and is therefore highly sensitive for the detection of thrombus. However, it views only the lesion surface and is not representative of the internal heterogeneity of the plaque. As a routine clinical tool, it may not be practical due to the thickness of the catheter and the invasiveness of this technique. U.S. Pat. No. 5,217,456 and U.S. Pat. No. 5,275,594 disclose the use of light that induces fluorescence in tissues, and of laser energy that stimulates fluorescence in non-calcified tissues. These types of devices differentiate healthy tissue from atherosclerotic plaque, but are not clinically useful for differentiating vulnerable plaque from less dangerous, stable plaque.

High-resolution, real-time B-mode ultrasonography with Doppler flow imaging (Duplex scanning) has merged as one of the best modalities for visualization of carotid arteries (Patel et al. *Stroke* 1995, 26, 1753–1758). Measurements of wall thickness and quantitative analysis of plaque mass and area can be determined. The echogenicity of the plaque reflects plaque characteristics; echoluscent heterogeneous plaque is associated with both intraplaque hemorrhage and lipids, whereas echodense homogeneous plaque is mostly a fibrous plaque. In addition, the configuration of the plaque (mural versus nodular) can identify active (mural) lesions that are more prone to proliferation and thromboembolism (Weinberger et al. *J. Am. Med. Assoc.* 1995, 12, 1515–1521). Because the technique is not invasive, it can be used to evaluate the efficacy of drug treatment and to study the natural history of atheroscolerosis (longitudinal studies) by follow-up of individuals at increased risk of atherosclerosis. In coronary and peripheral arteries of low extremities, however, Duplex scanning is clinically not as useful as the traditional angiography.

Atherosclerotic calcification is an organized and regulated process and is found more frequently in advanced lesions, although it may occur in small amount in early lesions (Erbel et al. *Eur. Heart J.* 2000, 21, 720–732; Wexler et al. *Circulation* 1996, 94, 1175–1192). There is a strong association between coronary calcium and obstructive coronary artery disease, and is clearly shown that the amount of coronary calcium was a useful predictor of the extent of coronary artery disease (Agatson et al. *J. Am. Coll. Cardiol.* 1990, 15, 827–832; Schmermund et al. *Am. J. Cardiol.* 2000, 86, 127–132; Budoff et al. *Am. J. Cardiol.* 2000, 86, 8–11). MRI, fluoroscopy, electron beam CT (EBCT), and helical CT can identify calcific deposits in blood vessels. However, only EBCT can quantitate the amount or volume of calcium (Wexler et al. *Circulation* 1996, 94, 1175–1192). In addition, the EBCT images of the myocardium can be obtained in 0.1 sec. Because of the rapid image acquisition time, motion artifacts are eliminated (Brundage et al. In: Fuster, V. (Ed.).

*Syndromes of Atherosclerosis: correlations of clinical imaging and pathology*. Armonk, N.Y.: Futura Publishing Company, Inc., 1996, 417–427). It has been well-documented that the presence of coronary artery calcium, detected by EBCT, may be a sensitive early marker for the presence and progression of atheroclerotic lesion before the development of complicated lesions (Janowitz et al. *Am. J. Cardiol.* 1993, 72, 247–254).

A major limitation using EBCT for the characterization of calcium in the plaque is reproducibility (Becker et al. *Eur. Radiol.* 2000, 10, 629–635). In particular the reproducibility of small and very small calcium scores (<100) is lower than that for higher score values. In addition, coronary calcium screening can not reveal atherosclerotic plaque that has little or no calcification-and such soft, lipid-rich plaques are perhaps the most dangerous of all, vulnerable to rupture as a result of hemodynamic stress or inflammation (Carrington, C. *Diagnostic Imaging*, 2000, (April), 48–53; Doherty et al. *Am. Heart J.* 1999, 137, 806–814).

As red blood cells and platelets gather at the site of the rupture, a blood clot forms and blocks the artery, causing a heart attack. Biologically, calcium may not be the ideal marker because a calcified lesion is presumably a stable lesion, less prone to rupture. More recent data show that coronary calcium scores do not seem to predict myocardial perfusion deficits, plaque burden, or cardiovascular events (Rumberger, J. A. *Circulation* 1998, 97, 2095–2097; Polak, J. F. *Radiology* 2000, 216, 323–324).

Magnetic resonance techniques using gradient echo methods to generate images of flowing blood as positive contrast within the lumen of vessels are similar to conventional angiography techniques (Doyle, M. and Pohost, G. In: Fuster, V. (Ed.). *Syndromes of Atherosclerosis: correlations of clinical imaging and pathology*. Armonk, N.Y.: Futura Publishing Company, Inc., 1996, 313–332; Grist, T. and Turski, P. A. In: Fuster, V. (Ed.). *Syndromes of Atherosclerosis: correlations of clinical imaging and pathology*. Armonk, N.Y.: Futura Publishing Company, Inc., 1996, 333–362). Magnetic resonance angiography (MRA) of coronary arteries is currently under development, and the resolution is within the range of 1 mm³. MRA techniques provide images of the vessel lumen, whereas MRI studies are often performed to evaluate the effects of the disease on the tissue supplied by the vessel. Recent developments in high-resolution (0.4 mm), fast spin-echo imaging and computer processing techniques visualize in vivo, atherosclerotic plaque activity and intimal thickening (Yuan et al. *J. Magn. Reson. Imaging* 1994, 4, 43–49).

In a recent clinical study in patients with carotid atherosclerosis, MRI was the first non-invasive imaging modality to allow the discrimination of lipid cores, fibrous caps, calcification, normal media, adventia, intraplaque hemorrhage, and acute thrombosis (Toussaint et al. *Atheroscler. Thromb.* 1995, 15, 1533–1542; Toussaint et al. *Circulation* 1996, 94, 932–938). The key advantage of contrast-enhanced rapid imaging techniques is the ability to provide detailed "functional information" with high accuracy (McVein, E. R. *Magn. Reson. Imaging* 1996, 14, 137–150; Glover, G. D. and Herfkins, R. J. *Radiology* 1998, 207, 289–235).

In the last two decades, many radiotracers have been developed based on several molecules and cell types involved in atherosclerosis. The potential utility of these radiotracers for imaging atherosclerotic lesions has been studied in animal models, and has been recently reviewed (Vallabhajosula, S. and Fuster, V. *J. Nucl. Med.* 1997, 38, 1788–1796; Cerqueira, M. D. *Seminars Nucl. Med.* 1999, 29, 339–351; Narula, J. *J. Nucl. Cardiol.* 1999, 6, 81–90; Narula, J. *Nucl. Med. Commun.* 2000, 21, 601–608). In general, radiolabeled proteins and platelets have shown some clinical potential as imaging agents of atherosclerosis, but due to poor target/background and target/blood ratios, these agents are not ideal for imaging coronary or even carotid lesions. Radiolabeled peptides, antibody fragments and metabolic tracers like FDG appear to offer new opportunities for nuclear scintigraphic techniques in the noninvasive imaging of atherothrombosis. However, noninvasive imaging of atherosclerosis remains a challenge for nuclear techniques mainly due to their intrinsic shortcomings, such as low resolution, compared to MRI and CT.

Most of these techniques identify some of the morphological and functional parameters of atherosclerosis and provide qualitative or semiquantitative assessment of the relative risk associated with the disease. Knowledge of the composition of an atherosclerotic plaque may provide a window on the progression of the lesion, which may result in the development of specific therapeutic strategies for intervention. However, these diagnostic procedures are either invasive or yield little information on the underlying pathophysiology such as cellular composition of the plaque, and biological characteristics of each component in the plaque at the molecular level.

As such, a non-invasive method to diagnose and monitor various cardiovascular diseases (e.g., atherosclerosis, vulnerable plaque, coronary artery disease, renal disease, thrombosis, transient ischemia due to clotting, stroke, myocardial infarction, organ transplant, organ failure and hypercholesterolemia) are needed. The non-invasive method should yield information regarding the underlying pathophysiology of the plaque, such as the cellular composition of the plaque and biological characteristics of each component in the plaque at the molecular level.

DETAILED DISCREPTION OF THE INVENTION

The principal mechanisms involved in atherogenesis are lipid infiltration, cellular invasion and proliferation and thrombus formation. Molecular imaging of atherosclerotic lesions is expected to target one of the three major components of plaque-lipid core, macrophage infiltration or proliferating smooth muscle cells (Ross, R. *Nature* 1993, 362, 801–809). Since predominance of any one component determines the behavior of the plaque, it is logical to assume that detection of an abundance of a given component will address the prognostic outcome of the plaque (Ross, R. *Nature* 1993, 362, 801–809). The presence of large necrotic lipid cores contributes to the vulnerability of plaque to rupture. The intense macrophage infiltration of the plaque leads to release of cytokines and matrix metalloproteinases and thereby renders the plaque prone to rupture. The prevalence of smooth muscle cells provide stability to the plaque, but rapid proliferation is associated with rapidly progressive luminal stenosis such as in post-angioplastic restenosis. Therefore, it is possible to selectively target one of these three components for molecular imaging of atherosclerosis.

Macrophages are known to play a significant role in the development of atherosclerosis. Macrophages down-regulate their LDL receptors and express mRNA and undergo new protein synthesis for a novel receptor for modified LDL. This receptor recognizes all modified forms of LDL and come to be known as the macrophage scavenger receptor (MSR). Numerous studies report the presence of the scavenger receptors, which bind to a broad range of molecules. It has been proposed that macrophage scavenger receptors play a key role in the development of atherosclerosis by mediating uptake of ox-LDL by macrophages in arterial walls.

The scavenger receptors have been divided into three classes. Class A scavenger receptors include type I and II macrophage scavenger receptors (SR-AI and SR-AII). Type I SR-A differs from type II SR-A in that it contains an additional C-terminal cysteine-rich domain. Class B scavenger receptors (SR-B) include Fatty Acid Translocase (CD36) and SR-B1. Class B scavenger receptors are also located on macrophages and possess affinities towards ox-LDL, apoptotic cells, and anionic phospholipids. Recently, a new class of scavenger receptor has been identified as Macrosialin (CD68).

The expression of SR-A is mainly confined to activated macrophages, which accumulate in areas of inflammation such as atherosclerotic plaque. In addition, the SR-A has also been shown to play a significant role in the inflammatory response in host defense, cellular activation, adhesion, and cell-cell interaction, which makes SR-A a multifunctional player in the atherosclerotic process. Therefore, SR-A can serve as a target and the biomolecules that bind to the SR-A receptor can be used as new imaging agents for the diagnosis of atherosclerosis, particularly vulnerable plaque.

The molecules binding to the SR-A are generally polyanionic macromolecules, including acetyl-LDL (acLDL), oxidized LDL (oxLDL), polyribonucleotides, polysaccharides, lipopolysaccharides, lipoteichoic acid dextran sulfate, and anionic phospholipids such as phosphatidylserine. Radiolabeled biomolecules binding to macrophages have been used for imaging atherosclerotic lesions in animal models, and some of them have been studied in humans. These include radiolabeled LDL and oxidized LDL (Atsma et al. *Atherosclerosis and Thrombosis* 1993, 13, 78–83; Iuliano et al. *Atherosclerosis* 1996, 126, 131–141) and Tc-99m-labeled diadenosine tetraphosphates (Elmaleh et al. *Proc. Natl. Acad. Sci. USA* 1998, 95, 691–695). It was found that the uptake of I-125-labeled LDL is due to the accumulation of oxidized LDL in macrophage and can be suppressed by administration of vitamin E, a known antioxidant. In patients with carotid atherosclerosis, the uptake of Tc-99m-LDL was seen in soft lesions rich in macrophages, whereas mature fibrocalcific plaque did not accumulate radiolabeled LDL (Lees et al. *Atherosclerosis* 1988, 8, 461–468; Virgolini et al. *Eur. J. Nucl. Med.* 1991, 18, 948–951).

Recently, a small-molecule, nonpeptide macrophage SR-A antagonist has been reported to have μM binding affinity for SR-A (Lysko et al. *J. Pharmacol. Exp. Ther.* 1999, 289, 1277–1285). PCT Patent applications WO 99/07382, WO 00/06147, and WO 00/03704 disclose a series of SR-A antagonists and their potential use in the treatment of cardiovascular diseases. Chart I shows the general structures of SR-A receptor antagonists disclosed in PCT patent applications WO 99/07382, WO 00/06147, and WO 00/03704. Synthesis of examples of these diamidediphenolate compounds have been disclosed (see, e.g., Anson et al. *J. Am. Chem. Soc.* 1986, 108, 6593–6605). However, the use of these SR-A antagonists or their metal chelates, formed either via direct binding of metal ions or through the attachment of a metal chelate, for the diagnosis or detection of atherosclerosis and vulnerable plaque is not disclosed.
Chart I. SR-A Receptor Antagonists Disclosed in PCT Patent Applications WO 99/07382, WO 00/06147, and WO 00/03704.

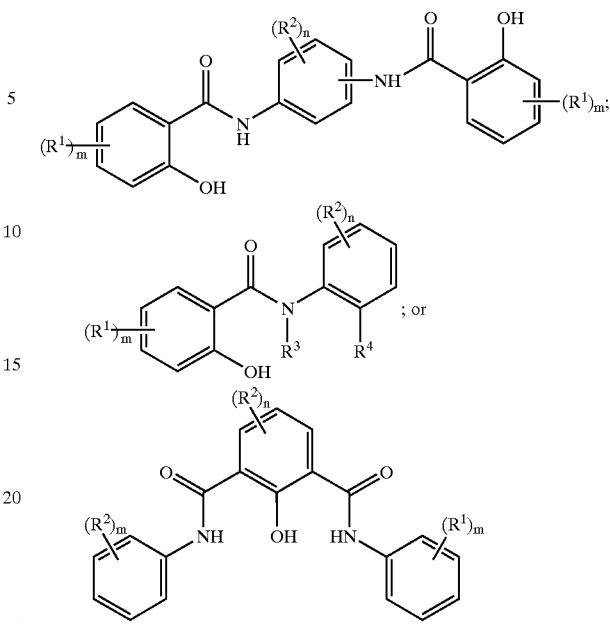

Therefore, one aspect of the present invention is a detectably labeled SR-A antagonist that is useful for the diagnosis and monitoring of various cardiovascular diseases (e.g., atherosclerosis, vulnerable plaque, coronary artery disease, renal disease, thrombosis, transient ischemia due to clotting, stroke, myocardial infarction, organ transplant, organ failure and hypercholesterolemia). The detectably labeled SR-A antagonist is useful as a radiopharmaceutical, an MRI imaging agent, or an X-ray contrast agent.

[1] One embodiment of the present invention provides a compound of formula (I):

$$M-C_h-L_n-(BM)_n \qquad (I)$$

wherein

M is a radionuclide selected from: $^{99m}$Tc, $^{117m}$Sn, $^{111}$In, $^{97}$Ru, $^{67}$Ga, $^{68}$Ga, $^{89}$Zr, $^{177}$Lu, $^{47}$Sc, $^{105}$Rh, $^{188}$Re, $^{60}$Cu, $^{62}$Cu, $^{64}$Cu and $^{67}$Cu, or a paramagnetic metal ion of atomic number 21–29, 42–44, or 58–70, or a heavy metal ion of atomic number 21–31, 39–49, 50, 56–80, 82, 83, 90;

$C_h$ is a metal chelator having a formula selected from the group:

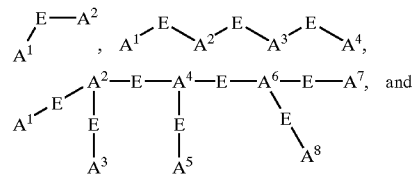

-continued

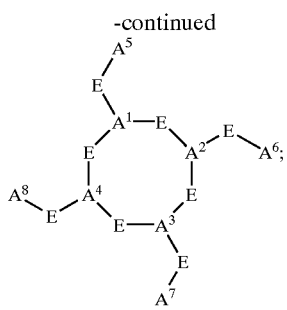

wherein $A^1$, $A^2$, $A^3$, $A^4$, $A^5$, $A^6$, $A^7$, and $A^8$ are independently selected at each occurrence from the group: $NR^{19}$, $NR^{19}R^{20}$, S, SH, O, OH, $PR^{19}$, $PR^{19}R^{20}$, $P(O)R^{21}R^{22}$, and a direct bond to $L_n$;

E is a direct bond, CH, or a spacer group independently selected at each occurrence from the group: $(C_1-C_{10})$alkyl substituted with 0–3 $R^{23}$, aryl substituted with 0–3 $R^{23}$, $(C_3-C_{10})$cycloalkyl substituted with 0–3 $R^{23}$, heterocyclo-$(C_1-C_{10})$alkyl substituted with 0–3 $R^{23}$, wherein the heterocyclo group is a 5–10 membered heterocyclic ring system containing 1–4 heteroatoms independently selected from N, S, and O, $(C_6-C_{10})$aryl-$(C_1-C_{10})$alkyl substituted with 0–3 $R^{23}$, $(C_1-C_{10})$alkyl-$(C_6-C_{10})$aryl-substituted with 0–3 $R^{23}$, and a 5–10 membered heterocyclic ring system containing 1–4 heteroatoms independently selected from N, S, and O and substituted with 0–3 $R^{23}$;

$R^{19}$ and $R^{20}$ are each independently selected from the group: a direct bond to $L_n$, hydrogen, $(C_1-C_{10})$alkyl substituted with 0–3 $R^{23}$, aryl substituted with 0–3 $R^{23}$, $(C_3-C_{10})$cycloalkyl substituted with 0–3 $R^{23}$, heterocyclo-$(C_1-C_{10})$alkyl substituted with 0–3 $R^{23}$, wherein the heterocyclo group is a 5–10 membered heterocyclic ring system containing 1–4 heteroatoms independently selected from N, S, and O, $(C_6-C_{10})$aryl-$(C_1-C_{10})$alkyl substituted with 0–3 $R^{23}$, $(C_1-C_{10})$alkyl-$(C_6-C_{10})$aryl-substituted with 0–3 $R^{23}$, a 5–10 membered heterocyclic ring system containing 1–4 heteroatoms independently selected from N, S, and O and substituted with 0–3 $R^{23}$, and an electron, provided that when one of $R^{19}$ or $R^{20}$ is an electron, then the other is also an electron;

$R^{21}$ and $R^{22}$ are each independently selected from the group: a direct bond to $L_n$, —OH, $(C_1-C_{10})$alkyl substituted with 0–3 $R^{23}$, $(C_1-C_{10})$alkyl substituted with 0–3 $R^{23}$, aryl substituted with 0–3 $R^{23}$, $(C_3-C_{10})$cycloalkyl substituted with 0–3 $R^{23}$, heterocyclo-$(C_1-C_{10})$alkyl substituted with 0–3 $R^{23}$, wherein the heterocyclo group is a 5–10 membered heterocyclic ring system containing 1–4 heteroatoms independently selected from N, S, and O, $(C_6-C_{10})$aryl-$(C_1-C_{10})$alkyl substituted with 0–3 $R^{23}$, $(C_1-C_{10})$alkyl-$(C_6-C_{10})$aryl-substituted with 0–3 $R^{23}$, and a 5–10 membered heterocyclic ring system containing 1–4 heteroatoms independently selected from N, S, and O and substituted with 0–3 $R^{23}$;

$R^{23}$ is independently selected at each occurrence from the group: a direct bond to $L_n$, =O, F, Cl, Br, I, —$CF_3$, —CN, —$CO_2R^{24}$, —$C(=O)R^{24}$, —$C(=O)N(R^{24})_2$, —CHO, —$CH_2OR^{24}$, —$OC(=O)R^{24}$, —$OC(=O)OR^{24a}$, —$OR^{24}$, —$OC(=O)N(R^{24})_2$, —$NR^{25}C(=O)R^{24}$, —$NR^{25}C(=O)OR^{24a}$, —$NR^{25}C(=O)N(R^{24})_2$, —$NR^{25}SO_2N(R^{24})_2$, —$NR^{25}SO_2R^{24a}$, —$SO_3H$, —$SO_2R^{24a}$, —$SR^{24}$, —$S(=O)R^{24a}$, —$SO_2N(R^{24})_2$, —$N(R^{24})_2$, —$NHC(=S)NHR^{24}$, =$NOR^{24}$, $NO_2$, —$C(=O)NHOR^{24}$, —$C(=O)$ $NHNR^{24}R^{24a}$, —$OCH_2CO_2H$, 2-(1-morpholino)ethoxy, $(C_1-C_5)$alkyl, $(C_2-C_4)$alkenyl, $(C_3-C_6)$cycloalkyl, $(C_3-C_6)$cycloalkylmethyl, $(C_2-C_6)$alkoxyalkyl, aryl substituted with 0–2 $R^{24}$, and a 5–10 membered heterocyclic ring system containing 1–4 heteroatoms independently selected from N, S, and O;

$R^{24}$, $R^{24a}$, and $R^{25}$ are independently selected at each occurrence from the group: a direct bond to $L_n$, H, $(C_1-C_6)$ alkyl, phenyl, benzyl, $(C_1-C_6)$alkoxy, halide, nitro, cyano, and trifluoromethyl;

$L_n$ is a linking group having the formula:

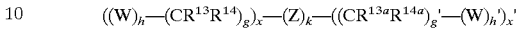

wherein,

W is independently selected at each occurrence from the group: O, S, NH, NHC(=O), C(=O)NH, $NR^{15}C(=O)$, C(=O)N $R^{15}$, C(=O), C(=O)O, OC(=O), NHC(=S)NH, NHC(=O)NH, $SO_2$, $SO_2NH$, $(OCH_2CH_2)_s$, $(CH_2CH_2O)_s{}'$, $(OCH_2CH_2CH_2)_s{}''$, $(CH_2CH_2CH_2O)_t$, and (aa)$_t{}'$;

aa is independently at each occurrence an amino acid;

Z is selected from the group: aryl substituted with 0–3 $R^{16}$, $(C_3-C_{10})$cycloalkyl substituted with 0–3 $R^{16}$, and a 5–10 membered heterocyclic ring system containing 1–4 heteroatoms independently selected from N, S, and O and substituted with 0–3 $R^{16}$;

$R^{13}$, $R^{13a}$, $R^{14}$, $R^{14a}$, and $R^{15}$ are independently selected at each occurrence from the group: H, =O, COOH, $SO_3H$, $PO_3H$, $(C_1-C_5)$alkyl substituted with 0–3 $R^{16}$, aryl substituted with 0–3 $R^{16}$, benzyl substituted with 0–3 $R^{16}$, and $(C_1-C_5)$alkoxy substituted with 0–3 $R^{16}$, $NHC(=O)R^{17}$, $C(=O)NHR^{17}$, $NHC(=O)NHR^{17}$, $NHR^{17}$, $R^{17}$, and a direct bond to $C_h$;

$R^{16}$ is independently selected at each occurrence from the group: a direct bond to $C_h$, $COOR^{17}$, $C(=O)NHR^{17}$, NHC $(=O)R^{17}$, OH, $NHR^{17}$, $SO_3H$, $PO_3H$, —$OPO_3H_2$, —$OSO_3H$, aryl substituted with 0–3 $R^{17}$, $(C_1-C_5)$alkyl substituted with 0–1 $R^{18}$, $(C_1-C_5)$alkoxy substituted with 0–1 $R^{18}$, and a 5–10 membered heterocyclic ring system containing 1–4 heteroatoms independently selected from N, S, and O and substituted with 0–3 $R^{17}$;

$R^{17}$ is independently selected at each occurrence from the group: H, alkyl substituted with 0–1 $R^{18}$, aryl substituted with 0–1 $R^{18}$, a 5–10 membered heterocyclic ring system containing 1–4 heteroatoms independently selected from N, S, and O and substituted with 0–1 $R^{18}$, $(C_3-C_{10})$cycloalkyl substituted with 0–1 $R^{18}$, polyalkylene glycol substituted with 0–1 $R^{18}$, carbohydrate substituted with 0–1 $R^{18}$, cyclodextrin substituted with 0–1 $R^{18}$, amino acid substituted with 0–1 $R^{18}$, polycarboxyalkyl substituted with 0–1 $R^{18}$, polyazaalkyl substituted with 0–1 $R^{18}$, peptide substituted with 0–1 $R^{18}$, wherein the peptide is comprised of 2–10 amino acids, 3,6-O-disulfo-B-D-galactopyranosyl, bis(phosphonomethyl)glycine, and a direct bond to $C_h$;

$R^{18}$ is a direct bond to $C_h$;

k is selected from 0, 1, and 2;

h is selected from 0, 1, and 2;

h' is selected from 0, 1, and 2;

g is selected from 0, 1, 2, 3, 4, 5, 6, 7, 8, 9, and 10;

g' is selected from 0, 1, 2, 3, 4, 5, 6, 7, 8, 9, and 10;

s is selected from 0, 1, 2, 3, 4, 5, 6, 7, 8, 9, and 10;

s' is selected from 0, 1, 2, 3, 4, 5, 6, 7, 8, 9, and 10;

s" is selected from 0, 1, 2, 3, 4, 5, 6, 7, 8, 9, and 10;

t is selected from 0, 1, 2, 3, 4, 5, 6, 7, 8, 9, and 10;

t' is selected from 0, 1, 2, 3, 4, 5, 6, 7, 8, 9, and 10;

x is selected from 0, 1, 2, 3, 4, and 5;

x' is selected from 0, 1, 2, 3, 4, and 5;

n is an integer from 1 to 10;

BM is an SR-A antagonist of formula:

[chemical structures]

wherein $R^1$ is independently selected from: H, $R^1$-benzamido, $R^1$-benzylether, $R^1$-benzylamino, amino, fluoralkyl, halo, cyano, nitro, aryloxyl, haloaryl, aryl, alkoxy, and 1,2-benzo; or $R^1$ represents a fused ring forming naphthalene moiety with the six membered aryl ring it substitutes;

$R^2$ is a direct bond to Ln; and m is an integer from 1 to 4;

or a pharmaceutically acceptable salt thereof.

[2] Another embodiment of the present invention provides a compound of embodiment [1] wherein $C_h$ is

[chemical structure]

wherein, $A^1$ is selected from the group: OH, and a direct bond to $L_n$;

$A^2$, $A^4$, and $A^6$ are each N;

$A^3$, $A^5$, and $A^8$ are each OH;

$A^7$ is a direct bond to $L_n$ or NH-bond to $L_n$;

E is a $C_2$ alkyl substituted with 0–1 $R^{23}$; and $R^{23}$ is =O.

[3] Another embodiment of the present invention provides a compound of embodiment [1] wherein $C_h$ is

[chemical structure]

wherein, $A^1$ is selected from the group: OH, and a direct bond to $L_n$;

$A^2$, $A^3$ and $A^4$ are each N;

$A^5$, $A^6$ and $A^8$ are each OH;

$A^7$ is a direct bond to $L_n$;

E is a $C_2$ alkyl substituted with 0–1 $R^{23}$; and $R^{23}$ is =O.

[4] Another embodiment of the present invention provides a compound of embodiment [1] wherein $C_h$ is

[chemical structure]

wherein $A^1$ is $NH_2$;

E is a direct bond;

$A^2$ is $NHR^{19}$;

$R^{19}$ is a heterocycle substituted with $R^{23}$, the heterocycle being selected from pyridine and pyrimidine;

$R^{23}$ is selected from a direct bond to $L_n$, $C(=O)NHR^{24}$ and $C(=O)R^{24}$;

$R^{24}$ is a direct bond to $L_n$;

$R^{30}$ is selected from the group: $-CO_2R^{31}$, $-OR^{31}$, $-SO_3H$, and $-N(R^{31})_2$; and $R^{31}$ is independently selected at each occurrence from the group: hydrogen and methyl.

[5] Another embodiment of the present invention provides a compound of embodiment [1] wherein $C_h$ is selected from the group: DTPA, DOTA, TETA, TRITA, HETA, DOTA-NHS, TETA-NHS, DOTA(Gly)3-L-(p-isothiocyanoto)-Phe-amide, and DO3A.

[6] Another embodiment of the present invention provides a compound of formula (I):

$$M-C_h-L_n-(BM)_n \quad (I)$$

wherein,

M is radionuclide selected from: $^{99m}Tc$, $^{117m}Sn$, $^{111}In$, $^{97}Ru$, $^{67}Ga$, $^{68}Ga$, $^{89}Zr$, $^{177}Lu$, $^{47}Sc$, $^{105}Rh$; $^{188}Re$, $^{60}Cu$, $^{62}Cu$, $^{64}Cu$ and $^{67}Cu$, or a paramagnetic metal ion of atomic number 21–29, 42–44, or 58–70, or a heavy metal ion of atomic number 21–31, 39–49, 50, 56–80, 82, 83, 90;

$C_h$ is a metal chelator having a formula selected from the group:

[chemical structures]

-continued

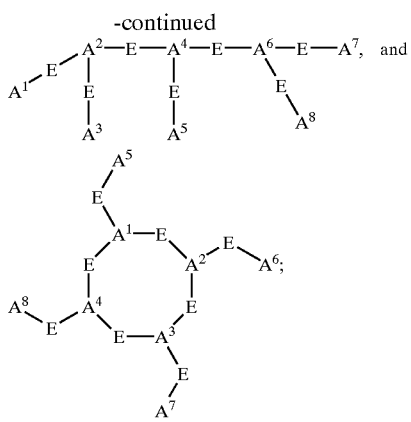

wherein, $A^1$, $A^2$, $A^3$, $A^4$, $A^5$, $A^6$, $A^7$, and $A^8$ are independently selected at each occurrence from the group: $NR^{19}$, $NR^{19}R^{20}$, S, SH, O, OH, $PR^{19}$, $PR^{19}R^{20}$, $P(O)R^{21}R^{22}$, and a direct bond to $L_n$;

E is a direct bond, CH, or a spacer group independently selected at each occurrence from the group: $(C_1-C_{10})$alkyl substituted with 0–3 $R^{23}$, aryl substituted with 0–3 $R^{23}$, $(C_3-C_{10})$cycloalkyl substituted with 0–3 $R^{23}$, heterocyclo-$(C_1-C_{10})$alkyl substituted with 0–3 $R^{23}$, wherein the heterocyclo group is a 5–10 membered heterocyclic ring system containing 1–4 heteroatoms independently selected from N, S, and O, $(C_6-C_{10})$aryl-$(C_1-C_{10})$alkyl substituted with 0–3 $R^{23}$, $(C_1-C_{10})$alkyl-$(C_6-C_{10})$aryl-substituted with 0–3 $R^{23}$, and a 5–10 membered heterocyclic ring system containing 1–4 heteroatoms independently selected from N, S, and O and substituted with 0–3 $R^{23}$;

$R^{19}$ and $R^{20}$ are each independently selected from the group: a direct bond to $L_n$, hydrogen, $(C_1-C_{10})$alkyl substituted with 0–3 $R^{23}$, aryl substituted with 0–3 $R^{23}$, $(C_1-C_{10})$cycloalkyl substituted with 0–3 $R^{23}$, heterocyclo-$(C_1-C_{10})$alkyl substituted with 0–3 $R^{23}$, wherein the heterocyclo group is a 5–10 membered heterocyclic ring system containing 1–4 heteroatoms independently selected from N, S, and O, $(C_6-C_{10})$aryl-$(C_1-C_{10})$alkyl substituted with 0–3 $R^{23}$, $(C_1-C_{10})$alkyl-$(C_6-C_{10})$aryl-substituted with 0–3 $R^{23}$, a 5–10 membered heterocyclic ring system containing 1–4 heteroatoms independently selected from N, S, and O and substituted with 0–3 $R^{23}$, and an electron, provided that when one of $R^{19}$ or $R^{20}$ is an electron, then the other is also an electron;

$R^{21}$ and $R^{22}$ are each independently selected from the group: a direct bond to $L_n$, —OH, $(C_1-C_{10})$alkyl substituted with 0–3 $R^{23}$, $(C_1-C_{10})$alkyl substituted with 0–3 $R^{23}$, aryl substituted with 0–3 $R^{23}$, $(C_3-C_{10})$cycloalkyl substituted with 0–3 $R^{23}$, heterocyclo-$(C_1-C_{10})$alkyl substituted with 0–3 $R^{23}$, wherein the heterocyclo group is a 5–10 membered heterocyclic ring system containing 1–4 heteroatoms independently selected from N, S, and O, $(C_6-C_{10})$aryl-$(C_1-C_{10})$alkyl substituted with 0–3 $R^{23}$, $(C_1-C_{10})$alkyl-$(C_6-C_{10})$aryl-substituted with 0–3 $R^{23}$, and a 5–10 membered heterocyclic ring system containing 1–4 heteroatoms independently selected from N, S, and O and substituted with 0–3 $R^{23}$;

$R^{23}$ is independently selected at each occurrence from the group: a direct bond to $L_n$, =O, F, Cl, Br, I, —$CF_3$, —CN, —$CO_2R^{24}$, —$C(=O)R^{24}$, —$C(=O)N(R^{24})_2$, —CHO, —$CH_2OR^{24}$, —$OC(=O)R^{24}$, —$OC(=O)OR^{24a}$, —$OR^{24}$, —$OC(=O)N(R^{24})_2$, —$NR^{25}C(=O)R^{24}$, —$NR^{25}C(=O)OR^{24a}$, —$NR^{25}C(=O)N(R^{24})_2$, —$NR^{25}SO_2N(R^{24})_2$, —$NR^{25}SO_2R^{24a}$, —$SO_3H$, —$SO_2R^{24a}$, —$SR^{24}$, —$S(=O)$ $R^{24a}$, —$SO_2N(R^{24})_2$, —$N(R^{24})_2$, —$NHC(=S)NHR^{24}$, =$NOR^{24}$, $NO_2$, —$C(=O)NHOR^{24}$, —$C(=O)$ $NHNR^{24}R^{24a}$, —$OCH_2CO_2H$, 2-(1-morpholino)ethoxy, $(C_1-C_5)$alkyl, $(C_2-C_4)$alkenyl, $(C_3-C_6)$cycloalkyl, $(C_3-C_6)$cycloalkylmethyl, $(C_2-C_6)$alkoxyalkyl, aryl substituted with 0–2 $R^{24}$, and a 5–10 membered heterocyclic ring system containing 1–4 heteroatoms independently selected from N, S, and O;

$R^{24}$, $R^{24a}$, and $R^{25}$ are independently selected at each occurrence from the group: a direct bond to $L_n$, H, $(C_1-C_{10})$ alkyl, phenyl, benzyl, $(C_1-C_{10})$alkoxy, halide, nitro, cyano, and trifluoromethyl;

$L_n$ is a linking group having the formula:

$((W)_h—(CR^{13}R^{14})_g—(Z)_k—((CR^{13a}R^{14a})_{g'}—(W)_{h'})_{x'}$;

wherein,

W is independently selected at each occurrence from the group: O, S, NH, NHC(=O), C(=O)NH, $NR^{15}C(=O)$, $C(=O)NR^{15}$, C(=O), C(=O)O, OC(=O), NHC(=S)NH, NHC(=O)NH, $SO_2$, $SO_2NH$, $(OCH_2CH_2)_s$, $(CH_2CH_2O)_{s'}$, $(OCH_2CH_2CH_2)_{s''}$, $(CH_2CH_2CH_2O)_t$, and $(aa)_{t'}$;

aa is independently at each occurrence an amino acid;

Z is selected from the group: aryl substituted with 0–3 $R^{16}$, $(C_3-C_{10})$cycloalkyl substituted with 0–3 $R^{16}$, and a 5–10 membered heterocyclic ring system containing 1–4 heteroatoms independently selected from N, S, and O and substituted with 0–3 $R^{16}$;

$R^{13}$, $R^{13a}$, $R^{14}$, $R^{14a}$, and $R^{15}$ are independently selected at each occurrence from the group: H, =O, COOH, $SO_3H$, $PO_3H$, $(C_1-C_5)$alkyl substituted with 0–3 $R^{16}$, aryl substituted with 0–3 $R^{16}$, benzyl substituted with 0–3 $R^{16}$, and $(C_1-C_5)$alkoxy substituted with 0–3 $R^{16}$, $NHC(=O)R^{17}$, $C(=O)NHR^{17}$, $NHC(=O)NHR^{17}$, $NHR^{17}$, $R^{17}$, and a direct bond to $C_h$;

$R^{16}$ is independently selected at each occurrence from the group: a direct bond to $C_h$, $COOR^{17}$, $C(=O)NHR^{17}$, $NHC(=O)R^{17}$, OH, $NHR^{17}$, $SO_3H$, $PO_3H$, —$OPO_3H_2$, —$OSO_3H$, aryl substituted with 0–3 $R^{17}$, $(C_1-C_5)$alkyl substituted with 0–1 $R^{18}$, $(C_1-C_5)$alkoxy substituted with 0–1 $R^{18}$, and a 5–10 membered heterocyclic ring system containing 1–4 heteroatoms independently selected from N, S, and O and substituted with 0–3 $R^{17}$;

$R^{17}$ is independently selected at each occurrence from the group: H, alkyl substituted with 0–1 $R^{18}$, aryl substituted with 0–1 $R^{18}$, a 5–10 membered heterocyclic ring system containing 1–4 heteroatoms independently selected from N, S, and O and substituted with 0–1 $R^{18}$, $(C_3-C_{10})$cycloalkyl substituted with 0–1 $R^{18}$, polyalkylene glycol substituted with 0–1 $R^{18}$, carbohydrate substituted with 0–1 $R^{18}$, cyclodextrin substituted with 0–1 $R^{18}$, amino acid substituted with 0–1 $R^{18}$, polycarboxyalkyl substituted with 0–1 $R^{18}$, polyazaalkyl substituted with 0–1 $R^{18}$, peptide substituted with 0–1 $R^{18}$, wherein the peptide is comprised of 2–10 amino acids, 3,6-O-disulfo-B-D-galactopyranosyl, bis (phosphonomethyl)glycine, and a direct bond to $C_h$;

$R^{18}$ is a direct bond to $C_h$;

k is selected from 0, 1, and 2;

h is selected from 0, 1, and 2;

h' is selected from 0, 1, and 2;

g is selected from 0, 1, 2, 3, 4, 5, 6, 7, 8, 9, and 10;

g' is selected from 0, 1, 2, 3, 4, 5, 6, 7, 8, 9, and 10;

s is selected from 0, 1, 2, 3, 4, 5, 6, 7, 8, 9, and 10;

s' is selected from 0, 1, 2, 3, 4, 5, 6, 7, 8, 9, and 10;

s" is selected from 0, 1, 2, 3, 4, 5, 6, 7, 8, 9, and 10;

t is selected from 0, 1, 2, 3, 4, 5, 6, 7, 8, 9, and 10;

t' is selected from 0, 1, 2, 3, 4, 5, 6, 7, 8, 9, and 10;

x is selected from 0, 1, 2, 3, 4, and 5;

x' is selected from 0, 1, 2, 3, 4, and 5;

n is an integer from 1 to 10;

BM is an SR-A antagonist of formula:

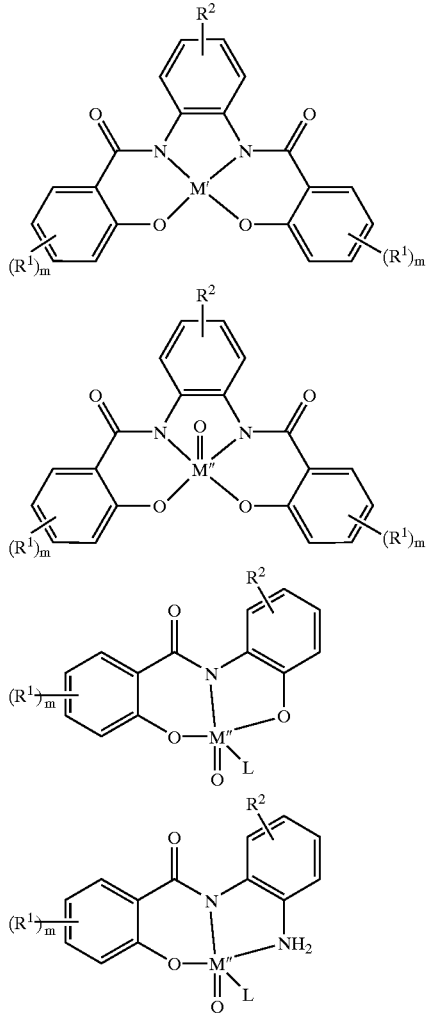

wherein $R^1$ is independently selected from: H, $R^1$-benzamido, $R^1$-benzylether, $R^1$-benzylamino, amino, fluoralkyl, halo, cyano, nitro, aryloxyl, haloaryl, aryl, alkoxy, and 1,2-benzo; or $R^1$ represents a fused ring forming naphthalene moiety with the six membered aryl ring it substitutes;

$R^2$ is a direct bond to Ln;

m is an integer from 1 to 4;

M' is a metal ion selected from Fe(III), Os(III), Co(III), Ni(II), or Cu(II);

M" is a metal-containing moiety selected from: V=O, Mo=O, or Re=O; and

L is a coligand selected from: trialkylphosphine, triarylphosphine, triarylalkylphosphine, pyridine or pyridine analog with appropriate substituent on the pyridine ring;

or a pharmaceutically acceptable salt thereof.

[7] Another embodiment of the present invention provides a compound of embodiment [6] wherein $C_h$ is

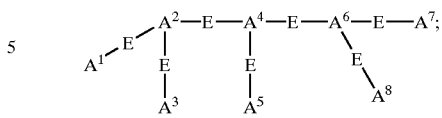

wherein, $A^1$ is selected from the group: OH, and a direct bond to $L_n$;

$A^2$, $A^4$, and $A^6$ are each N;

$A^3$, $A^5$, and $A^8$ are each OH;

$A^7$ is a direct bond to $L_n$ or NH-bond to $L_n$;

E is a $C_2$ alkyl substituted with 0–1 $R^{23}$; and $R^{23}$ is =O.

[8] Another embodiment of the present invention provides a compound of embodiment [6] wherein $C_h$ is

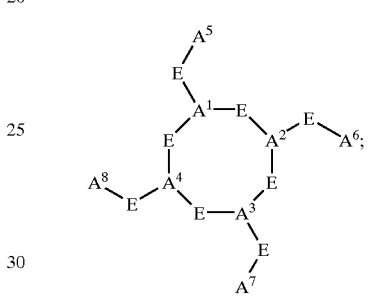

wherein, $A^1$ is selected from the group: OH, and a direct bond to $L_n$;

$A^2$, $A^3$ and $A^4$ are each N;

$A^5$, $A^6$ and $A^8$ are each OH;

$A^7$ is a direct bond to $L_n$;

E is a $C_2$ alkyl substituted with 0–1 $R^{23}$; and $R^{23}$ is =O.

[9] Another embodiment of the present invention provides a compound of embodiment [6] wherein $C_h$ is

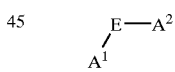

wherein, $A^1$ is $NH_2$;

E is a direct bond;

$A^2$ is $NHR^{19}$;

$R^{19}$ is a heterocycle substituted with $R^{23}$, the heterocycle being selected from pyridine and pyrimidine;

$R^{23}$ is selected from a direct bond to $L_n$, $C(=O)NHR^{24}$ and $C(=O)R^{24}$;

$R^{24}$ is a direct bond to $L_n$;

$R^{30}$ is selected from the group: $-CO_2R^{31}$, $-OR^{31}$, $-SO_3H$, and $-N(R^{31})_2$; and $R^{31}$ is independently selected at each occurrence from the group: hydrogen and methyl.

[10] Another embodiment of the present invention provides a compound of embodiment [6] wherein $C_h$ is selected from the group: DTPA, DOTA, TETA, TRITA, HETA, DOTA-NHS, TETA-NHS, DOTA(Gly) 3-L-(p-isothiocyanoto)-Phe-amide, and DO3A.

[11] Another embodiment of the present invention provides a compound of the formula:

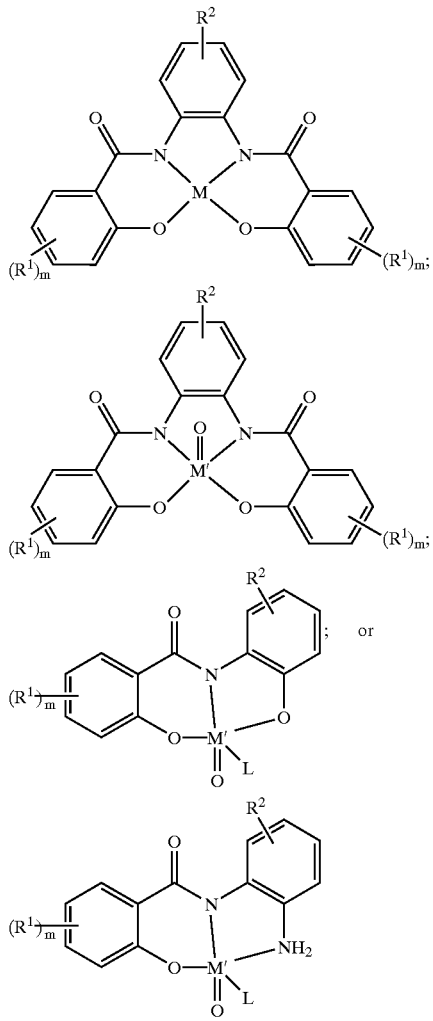

wherein

M is radionuclide selected from: $^{60}$Cu, $^{62}$Cu, $^{64}$Cu and $^{67}$Cu;

M' is $^{99m}$Tc or $^{188}$Re;

$R^1$ is independently selected from: H, $R^1$-benzamido, $R^1$-benzylether, $R^1$-benzylamino, amino, fluoralkyl, halo, cyano, nitro, aryloxyl, haloaryl, aryl, alkoxy, and 1,2-benzo; or $R^1$ represents a fused ring forming naphthalene moiety with the six membered aryl ring it substitutes;

$R^2$ is independently selected from: H, fluoralkyl, halo, aryloxyl, haloaryl, aryl, alkoxy, and 1,2-benzo; or $R^2$ represents a fused ring forming naphthalene moiety with the six membered aryl ring it substitutes;

m is an integer from 1 to 4; and

L is a coligand selected from: trialkylphosphine, triarylphosphine, triarylyalkylphosphine, pyridine or pyridine analog with appropriate substituent on the pyridine ring;

or a pharmaceutically acceptable salt thereof.

[12] Another embodiment of the present invention provides a method to diagnose a cardiovascular disease in a patient (e.g., human). The method comprises administering to the patient in need of such diagnosis an effective amount of a compound of embodiment [1], [2], [3], [4], or [5] and detecting the presence of the compound.

[13] Another embodiment of the present invention provides a method of embodiment [12] wherein the cardiovascular disease is selected from: atherosclerosis, vulnerable plaque, coronary artery disease, renal disease, thrombosis, transient ischemia due to clotting, stroke, myocardial infarction, organ transplant, organ failure and hypercholesterolemia.

[14] Another embodiment of the present invention provides a method to monitor a cardiovascular disease in a patient. The method comprises administering to the patient in need of such monitoring an effective amount of a compound of embodiment [1], [2], [3], [4], or [5] and detecting the presence of the compound.

[15] Another embodiment of the present invention provides the method of embodiment 14 wherein the cardiovascular disease is selected from: atherosclerosis, vulnerable plaque, coronary artery disease, renal disease, thrombosis, transient ischemia due to clotting, stroke, myocardial infarction, organ transplant, organ failure and hypercholesterolemia

[16] Another embodiment of the present invention provides a method to monitor the progression of an atherosclerotic lesion in a patient. The method comprises administering to the patient in need of such monitoring an effective amount of a compound of embodiment [1], [2], [3], [4], or [5] and detecting the presence of the compound.

[17] Another embodiment of the present invention provides a method to detect vulnerable plaque in a patient. The method comprises administering to the patient in need of such detection a compound of embodiment [1], [2], [3], [4], or [5] and detecting the presence of the compound.

[18] Another embodiment of the present invention provides a method of embodiment [12], [13], [14], [15], [16], or [17] wherein the detection comprises magnetic resonance imaging.

[19] Another embodiment of the present invention provides a method of embodiment [12], [13], [14], [15], [16], or [17] wherein the detection comprises X-ray imaging.

[20] Another embodiment of the present invention provides a method to diagnose a cardiovascular disease in a patient. The method comprises administering to the patient in need of such diagnosis an effective amount of a compound of embodiment [6], [7], [8], [9], or [10] and detecting the presence of the compound.

[21] Another embodiment of the present invention provides a method of embodiment 20 wherein the cardiovascular disease is selected from: atherosclerosis, vulnerable plaque, coronary artery disease, renal disease, thrombosis, transient ischemia due to clotting, stroke, myocardial infarction, organ transplant, organ failure and hypercholesterolemia.

[22] Another embodiment of the present invention provides a method to monitor a cardiovascular disease in a patient. The method comprises administering to the patient in need of such monitoring an effective amount of a compound of embodiment [6], [7], [8], [9], or [10] and detecting the presence of the compound.

[23] Another embodiment of the present invention provides a method of embodiment 22 wherein the cardiovascular disease is selected from: atherosclerosis, vulnerable plaque, coronary artery disease, renal disease, thrombosis, transient ischemia due to clotting, stroke, myocardial infarction, organ transplant, organ failure and hypercholesterolemia.

[24] Another embodiment of the present invention provides a method to monitor the progression of an atherosclerotic lesion in a patient. The method comprises administering to the patient in need of such monitoring an effective amount of a compound of embodiment [6], [7], [8], [9], or [10] and detecting the presence of the compound.

[25] Another embodiment of the present invention provides a method to detect vulnerable plaque in a patient. The method comprises administering to the patient in need of such detection a compound of embodiment [6], [7], [8], [9], or [10] and detecting the presence of the compound.

[26] Another embodiment of the present invention provides a method of embodiment [20], [21], [22], [23], [24], or [25] wherein the detection comprises magnetic resonance imaging.

[27] Another embodiment of the present invention provides a method of embodiment [20], [21], [22], [23], [24], or [25] wherein the detection comprises X-ray imaging.

[28] Another embodiment of the present invention provides a method of radio-imaging in a patient. The method comprises administering to a patient in need of such radio-imaging a compound of claim 11 and detecting the presence of the compound.

[29] Another embodiment of the present invention provides a pharmaceutical composition comprising a predetermined quantity of a compound of embodiment [1], [2], [3], [4], or [5], or a pharmaceutically acceptable salt thereof; and a pharmaceutically acceptable carrier or diluent.

[30] Another embodiment of the present invention provides a pharmaceutical composition of embodiment [29] further comprising an effective amount of a stabilizer.

[31] Another embodiment of the present invention provides a pharmaceutical composition of embodiment [30] wherein the stabilizer is selected from the group: ascorbic acid, benzyl alcohol, gentisic acid or a metal salt thereof, p-aminobenzoic acid or a salt thereof, cysteamine, 5-amino-2-hydroxybenzoic acid or a metal salt thereof, nicotinic acid or a metal salt thereof, nicotinamide, a polyhydroxylated aromatic compound, an aromatic amine, and a hydroxylated aromatic amine.

[32] Another embodiment of the present invention provides a pharmaceutical composition comprising a predetermined quantity of a compound of embodiment [6], [7], [8], [9], or [10], or a pharmaceutically acceptable salt thereof; and a pharmaceutically acceptable carrier or diluent.

[33] Another embodiment of the present invention provides a pharmaceutical composition of embodiment [32] further comprising an effective amount of a stabilizer.

[34] Another embodiment of the present invention provides a pharmaceutical composition of embodiment [33] wherein the stabilizer is selected from the group: ascorbic acid, benzyl alcohol, gentisic acid or a metal salt thereof, p-aminobenzoic acid or a salt thereof, cysteamine, 5-amino-2-hydroxybenzoic acid or a metal salt thereof, nicotinic acid or a metal salt thereof, nicotinamide, a polyhydroxylated aromatic compound, an aromatic amine, and a hydroxylated aromatic amine.

[35] Another embodiment of the present invention provides a pharmaceutical composition comprising a predetermined quantity of a compound of embodiment [11], or a pharmaceutically acceptable salt thereof; and a pharmaceutically acceptable carrier or diluent.

[36] Another embodiment of the present invention provides pharmaceutical composition of embodiment [35] further comprising an effective amount of a stabilizer.

[37] Another embodiment of the present invention provides a pharmaceutical composition of embodiment [36] wherein the stabilizer is selected from the group: ascorbic acid, benzyl alcohol, gentisic acid or a metal salt thereof, p-aminobenzoic acid or a salt thereof, cysteamine, 5-amino-2-hydroxybenzoic acid or a metal salt thereof, nicotinic acid or a metal salt thereof, nicotinamide, a polyhydroxylated aromatic compound, an aromatic amine, and a hydroxylated aromatic amine.

[38] Another embodiment of the present invention provides a kit comprising a sealed vial. The sealed vial comprises a predetermined quantity of a compound of embodiment [1], [2], [3], [4], or [5], or a pharmaceutically acceptable salt thereof; and a pharmaceutically acceptable carrier or diluent.

[39] Another embodiment of the present invention provides a kit of embodiment [38] further comprising at least one of a reducing agent, a bulking agent, and a weak transfer ligand.

[40] Another embodiment of the present invention provides a kit comprising a sealed vial. The sealed vial comprises a predetermined quantity of a compound of embodiment [6], [7], [8], [9], or [10], or a pharmaceutically acceptable salt thereof; and a pharmaceutically acceptable carrier or diluent.

[41] Another embodiment of the present invention provides a kit of embodiment [40] further comprising at least one of a reducing agent, a bulking agent, and a weak transfer ligand.

[42] Another embodiment of the present invention provides a kit comprising a sealed vial. The sealed vial comprises a predetermined quantity of a compound of embodiment [11] or a pharmaceutically acceptable salt thereof; and a pharmaceutically acceptable carrier or diluent.

[43] Another embodiment of the present invention provides a kit of embodiment [42] further comprising at least one of a reducing agent, a bulking agent, and a weak transfer ligand.

[44] Another embodiment of the present invention provides a kit comprising (a) a first vial comprising a predetermined quantity of a compound of embodiment [1], [2], [3], [4], or [5], or a pharmaceutically acceptable salt thereof; and (b) a second vial comprising a pharmaceutically acceptable carrier or diluent.

[45] Another embodiment of the present invention provides a kit of embodiment [44] further comprising at least one of a reducing agent, a bulking agent, and a weak transfer ligand.

[46] Another embodiment of the present invention provides a kit comprising (a) a first vial comprising a predetermined quantity of a compound of embodiment [6], [7], [8], [9], or [10], or a pharmaceutically acceptable salt thereof; and (b) a second vial comprising a pharmaceutically acceptable carrier or diluent.

[47] Another embodiment of the present invention provides a kit of embodiment [46] further comprising at least one of a reducing agent, a bulking agent, and a weak transfer ligand.

[48] Another embodiment of the present invention provides a kit comprising (a) a first vial comprising a predetermined quantity of a compound of embodiment [11], or a pharmaceutically acceptable salt thereof; and (b) a second vial comprising a pharmaceutically acceptable carrier or diluent.

[49] Another embodiment of the present invention provides a kit of embodiment [48] further comprising at least one of a reducing agent, a bulking agent, and a weak transfer ligand.

[50] Another embodiment of the present invention provides a compound of embodiment [1], [2], [3], [4], or [5] for use in medical therapy or diagnosis.

[51] Another embodiment of the present invention provides the use of a compound of embodiment [1], [2], [3], [4], or [5] as a radiopharmaceutical, as an MRI contrast agent, or as an X-ray contrast agent.

[52] Another embodiment of the present invention provides the use of a compound of embodiment [1], [2], [3], [4], or [5] for the manufacture of a medicament for diagnosing a cardiovascular disease in a patient or for monitoring a cardiovascular disease in a patient.

[53] Another embodiment of the present invention provides the use of a compound of embodiment [52] wherein the cardiovascular disease is selected from: atherosclerosis, vulnerable plaque, coronary artery disease, renal disease, thrombosis, transient ischemia due to clotting, stroke, myocardial infarction, organ transplant, organ failure and hypercholesterolemia.

[54] Another embodiment of the present invention provides the use of a compound of embodiment [1], [2], [3], [4], or [5] for the manufacture of a medicament for monitoring the progression of an atherosclerotic lesion or for detecting vulnerable plaque in a patient.

[55] Another embodiment of the present invention provides a compound of embodiment [6], [7], [8], [9], or [10] for use in medical therapy or diagnosis.

[56] Another embodiment of the present invention provides the use of a compound of embodiment [6], [7], [8], [9], or [10] as a radiopharmaceutical, as an MRI contrast agent, or as an X-ray contrast agent.

[57] Another embodiment of the present invention provides the use of a compound of embodiment [6], [7], [8], [9], or [10], for the manufacture of a medicament for diagnosing a cardiovascular disease in a patient or for monitoring a cardiovascular disease in a patient.

[58] Another embodiment of the present invention provides the use of a compound of embodiment [57] wherein the cardiovascular disease is selected from: atherosclerosis, vulnerable plaque, coronary artery disease, renal disease, thrombosis, transient ischemia due to clotting, stroke, myocardial infarction, organ transplant, organ failure and hypercholesterolemia.

[59] Another embodiment of the present invention provides the use of a compound of embodiment [6], [7], [8], [9], or [10] for the manufacture of a medicament for monitoring the progression of an atherosclerotic lesion or for detecting vulnerable plaque in a patient.

[60] Another embodiment of the present invention provides a compound of embodiment [11] for use in medical therapy or diagnosis.

[61] Another embodiment of the present invention provides the use of a compound of embodiment [11] as a radiopharmaceutical.

[62] Another embodiment of the present invention provides the use of a compound of embodiment [11] for the manufacture of a medicament for radio-imaging.

It is appreciated that certain features of the invention, which are, for clarity, described in the context of separate embodiments, may also be provided in combination in a single embodiment. Conversely, various features of the invention which are for brevity, described in the context of a single embodiment, may also be provided separately or in any subcombination.

The imaging agent disclosed in the present invention is an SR-A antagonist linked to a radioisotope, wherein the radioisotope is useful for gamma scintigraphy or positron emission tomography (PET). Alternatively, the SR-A targeting receptor antagonist is attached to a single or multiple paramagnetic metal chelates or superparamagnetic particles for magnetic resonance imaging (MRI). The SR-A binding molecules can also be bound to a phospholipid or polymer material that are used to encapsulate or stabilize microbubbles, which can be detectable by ultrasound imaging following localization at the site of tissue injury. Since SR-A is expressed by activated macrophages, which comprise 20–25% of the vulnerable plaque mass, the imaging agents disclosed in the present invention can be used for both detecting vulnerable plaque and monitoring the progression of the atherosclerotic lesion.

If the SR-A targeting biomolecule is linked to a radionuclide, the imaging agent can be used as a target-specific radiopharmaceutical. The radionuclide can be a gamma emitter such as Tc-99m for gamma scintigraphy or the radionuclide can be a positron emitter such as F-18 for PET imaging. If the radioisotope is metallic, the imaging agent is often called metalloradiopharmaceutical, which often contains four components: the SR-A antagonist targeting molecule, a linker, a bifunctional chelator (BFC), and the metallic radionuclide.

The SR-A receptor-targeting molecule serves as a vehicle. The SR-A receptor-targeting molecule carries the radionuclide to the receptor site on the activated macrophage. The SR-A receptor-targeting molecule can be a peptide, a peptidomimetic, or a non-peptide receptor ligand. The radionuclide is the radiation source for gamma scientigraphy or PET imaging. Between the SR-A receptor antagonist and the radionuclide is the bifunctional chelator (BFC), which binds strongly to the metal ion via several coordination bonds and is covalently attached to the targeting molecule either directly or through a linker. Selection of a BFC is largely determined by the nature and oxidation state of the metallic radionuclide. The linker can be a simple hydrocarbon chain, a long poly(ethylene glycol) (PEG), a poly anionic peptide sequence, or cationic peptide sequence, which is often used for modification of pharmacokinetics. In this invention, the use of a polyanionic peptide sequence may prove to be beneficial because polyanionic macromolecules are natural ligands for SR-A receptors. Sometimes, a metabolizeable linker is used to increase blood clearance and to reduce the background activity, thereby improving the target-to-background ratio.

Radionuclides, including but not limited to $^{18}$F, $^{99m}$Tc, $^{131}$I, $^{123}$I, $^{117m}$Sn, $^{111}$In, $^{67}$Ga, $^{68}$Ga, $^{89}$Zr, $^{62}$Cu $^{64}$Cu and $^{67}$Cu, have been proposed for diagnostic imaging. The choice of the radionuclide depends largely on the physical and nuclear properties (half-life and v-energy), availability, and cost. In general, generator-produced radionuclides are considered ideal, since the generator system consists of a long-lived parent isotope that decays to a short-lived daughter isotope. The daughter can be easily separated from the parent by either ion-exchange chromatography or solvent extraction.

Nearly 80% of radiopharmaceuticals used in nuclear medicine are $^{99m}$Tc-labeled compounds. The reason for such a preeminent position of $^{99m}$Tc in clinical use is its extremely favorable physical and nuclear characteristics. The 6 hour half-life is long enough to carry out radiopharmaceutical synthesis and to collect useful images. At the same time, it is short enough to permit the administration of millicurie amounts of $^{99m}$Tc radioactivity without significant radiation dose to the patient. The monochromatic 140 KeV photons are readily collimated to give images of superior spatial resolution. Furthermore, $^{99m}$Tc is readily available from commercial $^{99}$Mo-$^{99m}$Tc generators at low cost.

For $^{99m}$Tc-labeling of SR-A receptor antagonists, bifunctional chelators include $N_2S_2$ diaminedithiols, $N_2S_2$ diaminedithiols, $N_2S_2$ monoamidemonoamidedithiols, $N_3S$ aminediamidethiols, $N_3S$ triamidethiols, and HYNIC, which forms various ternary ligand systems when used in combination with tricine/water soluble phosphines, or tricine/pyridine analogs or tricine/substituted imime-N containing heterocycles. These ternary ligand systems have been disclosed in U.S. Pat. No. 5,744,120, U.S. Pat. No. 6,010,679, U.S. Pat. No. 5,879,659, and PCT Patent Application WO 98/53858. Various $^{99m}$Tc-labeling techniques have been described in several reviews (Liu, S. and Edwards, D. S. Chem. Rev. 1999, 99, 2235–2268; Jurisson, S. and Lydon, J. D. Chem. Rev. 1999, 99, 2205–2218; Anderson, C. J. and Welch, M. J. Chem. Rev. 1999, 99, 2219–2234; Volkert, W. A. and Hoffman, T. J. Chem. Rev. 1999, 99, 2269–2292; Liu et al. Bioconjugate Chem. 1997, 8, 621–636). After radiolabeling, the resulting reaction mixture may optionally be purified using one or more chromatographic methods, such as Sep-Pack or high performance liquid chromatography (HPLC). The preferred radiolabeling procedures are those, in which the chelation can be achieved without post-labeling purification.

This invention also provides a kit formulation for imaging atherosclerosis and vulnerable plaque. In general, a $^{99m}$Tc-based radiopharmaceutical kit contains an excess BFC-derivatized SR-A receptor antagonist relative to the amount of total technetium ($^{99m}$Tc and $^{99}$Tc) in order to achieve high radiolabeling yield, a reducing agent such as stannous chloride, if necessary, and other components such as a bulking agent or a weak transfer ligand. The kit may be provided in solution or in lyophilized form. Kits can be purchased and stored for daily preparation. In many cases, the $^{99m}$Tc-labeling can be accomplished simply by adding [$^{99m}$Tc]pertechnetate to the kit. The use of excess BFC-derivatized SR-A receptor antagonist should not cause blockage of the receptor binding of the radiolabeled SR-A antagonist. It also should not cause any side effects or unwanted pharmacological responses either.

For $^{111}$In and other metallic radionuclides, such as $^{67}$Ga, $^{68}$Ga, $^{89}$Zr, $^{62}$Cu, $^{64}$Cu and $^{67}$Cu, diethylenetriaminepentaacetic acid (DTPA), tetraazacyclododecane-1,4,7,10-tetracetic acid (DOTA) and their derivatives would be the candidates of choice as BFCs. The macrocyclic chelators such as DOTA are known to form highly stable metal chelates due to their highly preorganized macrocyclic ligand framework. DOTA and its derivatives have also been used as BFCs for the radiolabeling of proteins (antibodies or antibody fragments) and peptides with various diagnostic and therapeutic radionuclides (such as $^{111}$In and $^{90}$Y). Krejcarek and Tucker (Biochem. Biophys. Res. Commun. 1976, 77, 581–588) developed an activated DTPA analog via a mixed anhydride, which can be linked to proteins. Later, Hnatowich et al (Science 1983, 220, 613–616) used the cyclic anhydride of DTPA for the same purpose. These linear BFCs bond to various metal ions like In-111 and form thermodynamically stable metal chelates. However, metal chelates of linear BFCs are kinetically labile, which contributes to the loss of radionuclide from the metal chelate and often leads to severe bone marrow toxicity. Gansow et al (Bioconjugate Chem. 1991, 2, 187–194; Inorg. Chem. 1986, 25, 2772–2781) prepared a series of substituted DTPA analogs, which form metal chelates with improved solution stability.

Meares and coworkers were the first to synthesize macrocyclic BFCs (Anal. Biochem. 1985, 148, 249–253; Nucl. Med. Biol. 1986, 13, 311–318; J. Am. Chem. Soc. 1988, 110, 6266–6267), which form $^{67}$Cu and $^{90}$Y chelates with high thermodynamic stability and kinetic inertness. Macrocyclic chelants with three-dimensional cavities are of particular interest because of the high stability of the metal chelates, the substantial selectivity for certain metal ions, either by enforcing a specific spatial arrangement of donor atoms or by introducing different donor atoms into the ligand backbone, and their capability to adopt a preorganized conformation in the unchelated form. The higher the degree of preorganization of an unchelated ligand, the more stable the complex is.

For the last two decades, PET imaging was only used for academic research, most likely due the short half-life of isotopes, availability of generator systems, practicality of isotope production, transportation and distribution of the radiotracer. The development of outside vendors who can supply PET isotopes to a large number of local customers on a unit dose basis and the adaptability of SPECT cameras for PET imaging should start to increase the use of this imaging modality (Phelps, M. E. J. Nucl. Med. 2000, 41, 661–681; Bar-Shalom et al. Seminars Nucl. Med. 2000, 30, 150–185; O'Doherty, M. J. Nucl. Med. Commun. 2000, 21, 224–229; Nunan, T. O. and Hain, S. F. Nucl. Med. Commun. 2000, 21, 2229–233; Maisley, M. N. Nucl. Med. Commun. 2000, 21, 234–236; Barrington, S. F. Nucl. Med. Commun. 2000, 21, 237–240; Delbeke, D. J. Nucl. Med. 1999, 40, 1706–1715; Duncan, K. J. Nucl. Med. Technol. 1998, 26, 228–234; Haynes et al. J. Nucl. Med. 2000, 41, 309–314; Welch, M. and McCarthy, T. J. J. Nucl. Med. 2000, 41, 315–317).

Selection of a suitable isotope for PET imaging is a difficult task. In general, it is highly desirable the isotope does not have decays other than 511-keV positron emission. This will minimize the impairment of the spatial resolution due to energy and will reduce the radiation burden to the patient. A generator-based isotope is needed due to the high specific activity for receptor-based target specific radiopharmaceuticals. It is also much easier for transportation, delivery, and quality control using a generator produced isotope. The half-life of the parent isotope should be long while the half-life of the corresponding daughter isotope should be short. In addition, the cost for the production of the parent isotope and availability of the enriched source (for the production of the parent isotope) should also be considered.

$^{18}$F is a cyclotron-produced PET isotope. The relatively long half-life ($t_{1/2}$=110 min) makes it possible for regional suppliers to ship $^{18}$F-FDG radiotracers to the clinical sites and for clinicians to collect useful images. $^{18}$F can be readily incorporated into endogenous biological compounds such as 2-deoxo-D-glucose. Following the foot-step of MRI, recent developments of mobile trailers for FDG PET imaging has made it possible for small institutions to have access to state-of-art PET services.

If the PET isotope is $^{18}$F, the target-specific PET radiopharmaceutical can be readily prepared according to the known procedures (Vaidyanathan, G. and Zalutsky, M. R. Bioconjugate Chem. 1990, 1, 269–273; Vaidyanathan, G. and Zalutsky, M. R. Nucl. Med. Biol. 1992, 19, 275–281; Vaidyanathan, G. and Zalutsky, M. R. Bioconjugate Chem. 1994, 5, 352–364; Vaidyanathan, G. and Zalutsky, M. R. Nucl. Med. Biol. 1995, 22, 759–764; Sutcliffe-Goulden et al. Bioorg. Med. Chem. Lett. 2000, 10, 1501–1503). In general, an active $^{18}$F-containing intermediate, such as N-succinimidyl 4-[$^{18}$F]fluorobezoate, is prepared in high yield and high radiochemical purity, and is then conjugated to an amino group of the SR-A receptor antagonist to form the 4-[$^{18}$F]fluorobenzoyl conjugate. The $^{18}$F-labeled SR-A receptor antagonist can be readily purified by simple filtration, by regular column chromatography, or by HPLC either using a size-exclusion or by reverse phase. The preferred procedure is that in which the $^{18}$F-labeled SR-A receptor antagonist can be prepared in high specific activity and high radiochemical purity.

Another aspect of this invention is related to a stable radiopharmaceutical compositions comprising an effective amount of one or more stabilizers selected from ascorbic acid, benzyl alcohol, gentisic acid or its metal salts, p-aminobenzoic acid or its salt forms, cysteamine, 5-amino-2-hydroxybenzoic acid or its metal salt forms, nicotinic acid or its metal salt, nicotinamide, polyhydroxylated aromatic compounds, aromatic amines, and hydroxylated aromatic amines.

Nuclear magnetic resonance (NMR) is based on the absorption of radio-frequency energy by the magnetic moment of atomic nuclei in samples placed in a strong magnetic field. Conventional magnetic resonance imaging (MRI) of human body relies mainly on the detection of most abundant type of nuclei, the hydrogen in water (and to some extent, fat). For the discrimination of healthy and diseased tissues, adequate contrast is essential. Such contrast depends not only on differences in water concentration, but also on the NMR relaxation times $T_1$ and $T_2$, which in turn are related to local mobility and interactions. The MRI contrast agent is used to improve diagnosis of disease by changing tissue signal intensity. Contrast agents increase both $1/T_1$ and $1/T_2$ to varying degrees depending on their nature as well as the applied magnetic field. Agents such as gadolinium(III) that increase $1/T_1$ and $1/T_2$ by roughly similar amounts are best visualized using $T_1$-weighted images since the percentage change in $1/T_1$ in tissue is much greater than that in $1/T_1$ (Caravan et al. *Chem. Rev.* 1999, 99, 2293–2352). Iron-oxide particles generally lead to a much larger increase in $1/T_2$ than in $1/T_1$ and are best seen with in $T_2$-weighted scans.

MRI diagnosis is a relatively new and rapidly growing imaging modality. In just 20-years time, it has become a widely accepted diagnostic modality for a variety of diseases. When compared to other contrast agents, the MRI contrast agents are superior in concentration resolution in tissues. In addition, the use of MRI contrast agents does not involve exposure to X-rays or gamma radiation. The gadolinium chelates have proved to be an exceptionally well-tolerated class of contrast media. In particular, gadolinium MRI contrast agents do not show any nephrotoxicity in distinction to the iodinated contrast media for CT (Runge, V. M. *J. Magn. Reson. Imaging* 2000, 12, 205–213).

Generally, the more specific the accumulation of a contrast agent within the target tissue without distribution to surrounding tissue, the better the resulting lesion-tissue contrast. There are several approaches in pursuing better delivery of contrast agents to target tissues. In the conventional approach, efforts are directed toward the search and synthesis of molecules with site specific accumulation. Examples of this approach include Gd-porphyrin complexes and Gd-EOB-DTPA (Eovist: EOB-DTPA= ethyoxybenzyldiethlenetriaminepentaacetic adis), which is a paramagnetic heptobilliary contrast agent characterized by a high biliary excretion fraction and a predominant effect on the MR signal intensity of liver parenchyma (Stern et al. *Acta Radiologica* 2000, 41, 255–262). However, diagnostically profitable target/background ratios of these compounds are relatively low due to their low specificity.

The alternative approach is the use of magnetic labels, which accumulate at the desired site by the use of target specific carrier molecules. Optimally, the target should be an organ of sufficient size for MRI, and have a large number of specific binding sites and high blood flow. The targeting biomolecules include antibodies, antibody fragments, peptides, polysacchrides, non-peptide receptor ligands, and liposomes, which have been reviewed (Weissleder et al. *Magnetic Resonance Quarterly* 1992, 8, 55–63; Caravan et al. *Chem. Rev.* 1999, 99, 2293–2352).

Conceptually, the development of target-specific paramagnetic contrast agent uses the combination of high resolution of MRI technology and the high specificity of targeting biomolecules (e.g., antibodies, antibody fragments, peptides, polysacchrides, non-peptide receptor ligands, and liposomes). The major challenge in developing such a target-specific contrast agent is to deliver a sufficient amount of paramagnetic metal chelate or supermagnetic iron-oxide particles into the diseased tissue.

One approach to enhance the accumulation of the contrast agent is to use a peptide-mediated cellular delivery mechanism. Many peptide- and protein-mediated delivery systems have been used for cellular delivery of genes or virus for gene therapy, and have been reviewed (Lindgren et al. *Treads in Pharmaceutical Sciences* 2000, 21, 99–103; Schwartz, J. J. and Zhang, S. -Y. *Current Openions in Molecular Therapeutics* 2000, 2, 162–167). In the past five years, several peptides have been demonstrated to translocate across the plasma membrane of eukaryotic cells by a seemingly energy-independent pathway. Although the mechanism of entry into cells often remains unknown, these cell-penetrating peptides have been used successfully to internalize macromolecules (e.g., proteins) with molecular weights several time greater than their own (Fawell et al. *Proc. Natl. Acad. Sci. U.S.A.* 1994, 91, 664–668; Bayley, H. *Nat. Biotechnol.* 1999, 17, 1066–1067), peptides (Lin et al. *J. Biol. Chem.* 1995, 270, 14255–14258; Schluesenner, H. J. *J. Neurosci. Res.* 1996, 46, 258–262), antisence oligonucleotides (Morris et al. *Nucleic Acids Res.* 1997, 25, 2730–2736; Antopolsky et al. *Bioconjugate Chem.* 1999, 10, 598–606), peptide nucleic acid (Pooga, M. *Nat. Biotechnol.* 1998, 16, 857–861), and plamid DNA (Singh et al. *Bioconjugate Chem.* 1999, 10, 745–754). Recently, HIV-TAT peptide has been used for internalization of macrocyclic gadolinium chelates into mammalian cells (Bhorde et al. *Bioconjugate Chem.* 2000, 11, 301–305). The same HIV-TAT peptide has also been used for internalization of magnetic nanoparticles into lymphocytes from mouse spleen (Josephson et al. *Bioconjugate Chem.* 1999, 10, 186–191) or mouse neural progenitor cells (Lewin et al. *Nat. Biotechnol.* 2000, 17, 410–414). PCT Patent Application WO 99/67284 discloses the use of a cell membrane-permeant peptide-derivatized diagnostic pharmaceutical with the diagnostic label being a radionuclide or a paramagnetic metal ion.

If the SR-A receptor antagonist is linked to a paramagnetic metal ion such as $Gd^{3+}$, or superparamagnetic iron-oxide particle, the imaging agent could be used as a target-specific MRI contrast agent. Like indium, lanthanide metal ions also form highly stable metal chelates with DTPA, DOTA, as well as their derivatives (DTPA and DOTA chelates have been extensively reviewed recently (Liu S. and Edwards D. S. Bioconjugate Chemistry, 2001, 12, 7–34. For DTPA- and DOTA-related chelators, there are three possible approaches for derivatization and attachment of an SR-A receptor antagonist. In the first approach, the derivatization or attachment is at one of the carbon atoms of the chelator backbone. In the second approach, the derivatization or attachment is at the methylene-carbon atom of the acetate chelating arm. In these approaches, the derivatization or conjugation of the biomolecule does not lead to a significant change in the thermodynamic stability and kinetic inertness of the metal chelate. In the third approach, the derivatization or conjugation is at one of the acetate groups via a CO—N amide bond. Compared to the carboxylate-O, the carbonyl-O is a relatively weak donor for yttrium and lanthanide metal ions. This often leads to the lower thermodynamic stability of the corresponding metal chelate. However, the kinetic inertness of its metal complex remains relatively unchanged.

In U.S. Pat. No. 4,678,667, Meares et al disclosed a copper chelate conjugate for diagnostic or therapeutic applications. The bifunctional macrocyclic chelants include substituted DOTA, TETA, TRITA, and HETA. The linker is at least 8-atom in length and the attachment position of the linker is on the carbon atom of the polyamine macrocycle. U.S. Pat. No. 5,428,156 disclosed a method of producing DOTA, TETA, DOTA-NHS(NHS=N-hydroxysuccinimide) and TETA-NHS esters for conjugation of biomolecule. Meares et al (PCT Patent Application No. WO 95/26206 and U.S. Pat. No. 5,958,374) also disclosed a method for preparing a radionuclide-labeled chelating agent complex. It specifically disclosed DOTA$(Gly)_3$-L-(p-isothiocyanato)-Phe-amide as the BFC. The pendant linkers also include —$CH_2CO$—$(AA)_m$-(AA-Phe-Gly), where AA represents an amino acid diradical, more preferably the glycine diradical —$NHCH_2CO$—. Gansow et al (PCT Patent Application WO 89/11475, PCT Patent Application No. WO 91/14458, U.S. Pat. No. 4,923,985 and U.S. Pat. No. 5,428,154) disclosed a process of making 4-aminophenyl-DOTA and its use a BFC for the radiolabeling of biomolecules such as antibodies. Parker et al (PCT Patent Application No. WO 87/05030, PCT Patent Application No. WO89/01476, European Patent No. 0382583B1 and European Patent No. 0382583A1) disclosed a series of DOTA analogs as BFCs, which are coupled with biomolecules such as a protein, especially antibodies, peptides or carbohydrates to form conjugate compounds. The linker and conjugation group is attached to either one of the four acetate chelating arms or to one of the carbon atoms of the macrocyclic backbone. Watson, et al (PCT Patent Application No. WO 9012050 and PCT Patent Application No. WO9306868) disclosed polychelants and their metal chelates useful in diagnostic imaging and in radiotherapy. The macrocyclic chelant moieties are linked to the backbone moiety (dendrimer or polylysine) via an amide-bond. U.S. Pat. No. 5,053,053 disclosed a series of DOTA and DO3A analogs as BFCs. For DO3A-based BFCs, the conjugation group is connected to a linker attached to one of the four amine-nitrogen atoms. For DOTA derivatives, the linker group is connected to either one of the carbon-atoms on the macrocyclic backbone or to the methylene-carbon atom of one of the four acetate chelating arms. Tweedle et al (European Patent 0292689 A2; U.S. Pat. No. 4,885,363, U.S. Pat. No. 5,474,756, and U.S. Pat. No. 5,846,519) disclosed metal chelates, particularly those of neutral charge, for MRI contrast imaging. It also disclosed DO3A analogs as BFCs for the radiolabeling of biomolecules. Kruper et al (U.S. Pat. Nos. 5,310,535 and 5,739,323) disclosed the DOTA analogs as BFCs for the radiolabeling of proteins. The linker is connected to the acetate chelating arm and the conjugation group is on a benzene ring. It was shown that the DOTA monoamide has better kinetic inertness because of less bone uptake. Kubomura et al (Australian Patent No. 9335519 and European Patent No. 0565930A1) disclosed the use of DO3A—$CH_2CONHCH_2CH_2NH_2$ as the BFC, and the metal chelates of BFC-BM conjugates as diagnostic or therapeutic pharmaceuticals. Gozzin et al (PCT Patent Application No. WO 97/32862) disclosed a new class of polychelants, their chelates with metal ions and their physiologically acceptable salts, which can be used, either as they are or in association or formulation with other components, for diagnostic imaging in general or specific contrast agents for specific tissues, organs or body compartments. It specifically discloses DOTA as the BFC, and a process of making these macrocyclic chelants with DO3A-$CH_2CONHCH_2CH_2CHO$ and poly(amino acids) as key intermediates. Wilson et al (U.S. Pat. No. 5,756,065) also disclosed DOTA analogs as BFCs. The conjugation group is attached to a benzene ring and the linker group is connected to one of the four acetate chelating arms.

Definitions

The compounds described herein may have one or more asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention.

The term "substituted," as used herein, means that any one or more hydrogens on the designated atom is replaced with a selection from the indicated group, provided that the designated atom's normal valency is not exceeded, and that the substitution results in a stable compound. When a substitent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include Carbon-13 and Carbon-14.

When any variable (e.g., $R^1$) occurs more than one time in any constituent or formula for a compound, its definition at each occurrence is independent of its definition at every other occurrence. Thus, for example, if a group is shown to be substituted with 0–2 $R^1$, then the group may optionally be substituted with up to two $R^1$ groups and $R^1$ at each occurrence is selected independently from the definition of $R^1$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" is intended to include both branched and straight-chain saturated aliphatic hydrocarbon groups having the specified number of carbon atoms. Examples of alkyl include, but are not limited to, methyl, ethyl, n-propyl, i-propyl, n-butyl, s-butyl, t-butyl, n-pentyl, and s-pentyl. "Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, and pentachloroethyl. "Alkoxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. "Cycloalkyl" is intended to include saturated ring groups, such as cyclopropyl, cyclobutyl, or cyclopentyl. Alkenyl" is intended to include hydrocarbon chains of either a straight or branched configuration and one or more unsaturated carbon-carbon bonds which may occur in any stable point along the chain, such as ethenyl and propenyl. "Alkynyl" is intended to include hydrocarbon chains of either a straight or branched configuration and one or more triple carbon-carbon bonds which may occur in any stable point along the chain, such as ethynyl and propynyl.

"Halo" or "halogen" as used herein refers to fluoro, chloro, bromo, and iodo; and "counterion" is used to represent a small, negatively charged species such as chloride, bromide, hydroxide, acetate, and sulfate.

As used herein, "carbocycle" or "carbocyclic residue" is intended to mean any stable 3- to 7-membered monocyclic or bicyclic or 7- to 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane, [2.2.2] bicyclooctane, fluorenyl, phenyl, naphthyl, indanyl, adamantyl, and tetrahydronaphthyl.

As used herein, the term "heterocycle" or "heterocyclic system" is intended to mean a stable 5- to 7-membered monocyclic or bicyclic or 7- to 10-membered bicyclic heterocyclic ring which is saturated partially unsaturated or unsaturated (aromatic), and which consists of carbon atoms and from 1 to 4 heteroatoms independently selected from the group consisting of N, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic system" or "heteroaryl" is intended to mean a stable 5- to 7-membered monocyclic or bicyclic or 7- to 10-membered bicyclic heterocyclic aromatic ring which consists of carbon atoms and from 1 to 4 heterotams independently selected from the group consisting of N, O and S. It is preferred that the total number of S and O atoms in the aromatic heterocycle is not more than 1.

Examples of heterocycles include, but are not limited to, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro [2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2, 4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2, 3-triazolyl, 1,2,4-triazolyl, 1,2,5-triazolyl, 1,3,4-triazolyl, and xanthenyl. Preferred heterocycles include, but are not limited to, pyridinyl, furanyl, thienyl, pyrrolyl, pyrazolyl, pyrrolidinyl, imidazolyl, indolyl, benzimidazolyl, 1H-indazolyl, oxazolidinyl, benzotriazolyl, benzisoxazolyl, oxindolyl, benzoxazolinyl, and isatinoyl. Also included are fused ring and spiro compounds containing, for example, the above heterocycles.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

Since prodrugs are known to enhance numerous desirable qualities of pharmaceuticals (e.g., solubility, bioavailability, manufacturing, etc.) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers which release an active parent drug of the present invention in vivo when such prodrug is administered to a mammalian subject. Prodrugs of the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate and benzoate derivatives of alcohol and amine functional groups in the compounds of the present invention.

"Stable compound" and "stable structure" are meant to indicate a compound that is sufficiently robust to survive isolation to a useful degree of purity from a reaction mixture, and formulation into an efficacious therapeutic agent.

The coordination sphere of the radionuclide includes all the ligands or groups bound to the radionuclide. For a metalllic radionuclide to be stable, the metalllic radionuclide typically has a coordination number (number of donor atoms) comprised of an integer greater than or equal to 4 and less than or equal to 9; that is, there are 4 to 9 atoms bound to the metal and it is said to have a complete coordination sphere. The requisite coordination number for a stable radionuclide complex is determined by the identity of the radionuclide, its oxidation state, and the type of donor atoms. If the chelant does not provide all of the atoms necessary to stabilize the metal radionuclide by completing its coordination sphere, the coordination sphere is completed by donor atoms from other ligands, termed ancillary or co-ligands, which can also be either terminal or chelating.

Lyophilization aids useful in the preparation of diagnostic kits that are useful for the preparation of radiopharmaceuticals include but are not limited to mannitol, lactose, sorbitol, dextran, Ficoll, and polyvinylpyrrolidine (PVP).

Stabilization aids useful in the preparation of radiopharmaceuticals and in diagnostic kits that are useful for the preparation of the radiopharmaceuticals include but are not limited to ascorbic acid, cysteine, monothioglycerol, sodium bisulfite, sodium metabisulfite, gentisic acid, and inositol.

Solubilization aids useful in the preparation of radiopharmaceuticals and in diagnostic kits that are useful for the preparation of the radiopharmaceuticals include but are not limited to ethanol, glycerin, polyethylene glycol, propylene glycol, polyoxyethylene sorbitan monooleate, sorbitan monooleate, polysorbates, poly(oxyethylene)poly (oxypropylene)poly(oxyethylene) block copolymers (Pluronics) and lecithin. Preferred solubilizing aids are polyethylene glycol, and Pluronics.

Bacteriostats useful in the preparation of radiopharmaceuticals and in diagnostic kits that are useful for the preparation of the radiopharmaceuticals include but are not limited to benzyl alcohol, benzalkonium chloride, chlorbutanol, and methyl, propyl or butyl paraben.

Utility

The diagnostic radiopharmaceuticals are administered by intravenous injection, usually in saline solution, at a dose of 1 to 100 mCi per 70 kg body weight, or preferably at a dose of 5 to 50 mCi. Imaging is performed using known procedures.

The magnetic resonance imaging contrast agents of the present invention may be used in a similar manner as other MRI agents as described in U.S. Pat. Nos. 5,155,215; 5,087,440; Margerstadt et al. *Magn. Reson. Med.* 1986, 3, 808–812; Runge et al. *Radiology* 1988, 166, 835–838; and Bousquet et al. *Radiology* 1988, 166, 693–698. Generally, sterile aqueous solutions of the contrast agents are administered to a patient intravenously in dosages ranging from 0.01 to 1.0 mmoles per kg body weight.

For use as X-ray contrast agents, the compositions of the present invention should generally have a heavy atom concentration of 1 mM to 5 M, preferably 0.1 M to 2 M. Dosages, administered by intravenous injection, will typically range from 0.5 mmol/kg to 1.5 mmol/kg, preferably 0.8 mmol/kg to 1.2 mmol/kg. Imaging is performed using known techniques, preferably X-ray computed tomography.

Other features of the invention will become apparent in the course of the following descriptions of exemplary embodiments, which are given for illustration of the invention and are not intended to be limiting thereof.

The radiopharmaceuticals of the present invention comprised of a gamma emitting isotope are useful for imaging atherosclerosis, vulnerable plaque, coronary artery disease, renal disease, thrombosis, transient ischemia due to clotting, stroke, myocardial infarction, organ transplant, organ failure and hypercholesterolemia.

The radiopharmaceuticals of the present invention comprised of a positron emitting isotope are useful for imaging atherosclerosis, vulnerable plaque, coronary artery disease, renal disease, thrombosis, transient ischemia due to clotting, stroke, myocardial infarction, organ transplant, organ failure and hypercholesterolemia.

The compounds of the present invention comprised of one or more paramagnetic metal ions selected from gadolinium, dysprosium, iron, and manganese, are useful as contrast agents for magnetic resonance imaging (MRI) of atherosclerosis, vulnerable plaque, coronary artery disease, renal disease, thrombosis, transient ischemia due to clotting, stroke, myocardial infarction, organ transplant, organ failure and hypercholesterolemia.

The compounds of the present invention comprised of one or more heavy atoms with atomic number of 20 or greater are useful as X-ray contrast agents for X-ray imaging of atherosclerosis, vulnerable plaque, coronary artery disease, renal disease, thrombosis, transient ischemia due to clotting, stroke, myocardial infarction, organ transplant, organ failure and hypercholesterolemia.

The compounds of the present invention comprised of an echogenic gas containing surfactant microsphere are useful as ultrasound contrast agents for sonography of atherosclerosis, vulnerable plaque, coronary artery disease, renal disease, thrombosis, transient ischemia due to clotting, stroke, myocardial infarction, organ transplant, organ failure and hypercholesterolemia.

A number of reaction schemes can be used to attach the MMP inhibitors, Q, to the surfactant microsphere, $X^3$. These are illustrated in following reaction schemes where $S_f$ represents a surfactant moiety that forms the surfactant microsphere.

Acylation Reaction:

$$S_f{-}C(=O){-}Y+Q{-}NH_2 \text{ or } \rightarrow S_f{-}C(=O){-}NH{-}Q \quad Q{-}OH \text{ or } S_f{-}C(=O){-}O{-}Q$$

Y is a leaving group or active ester

Disulfide Coupling:

$$S_f{-}SH+Q{-}SH \rightarrow S_f{-}S{-}S{-}Q$$

Sulfonamide Coupling:

$$S_f{-}S(=O)_2{-}Y+Q{-}NH_2 \rightarrow S_f{-}S(=O)_2{-}NH{-}Q$$

Reductive Amidation:

$$S_f{-}CHO+Q{-}NH_2 \rightarrow S_f{-}NH{-}Q$$

In these reaction schemes, the substituents $S_f$ and Q can be reversed as well.

Representative compounds of the present invention were tested in the following in vitro and in vivo assays and models and were found to be active.

Di-AcLDL Uptake Assay

A high throughput assay (Freeman et al. *Proc. Natl. Sci. USA* 1991, 88, 4931–4935; Lysko et al. *J. Pharmacol. Exp. Ther.* 1999, 289, 1277–1285; PCT patent applications WO 99/07382, WO 00/06147, and WO 00/03704) was used for assessment of binding activity of SA-R antagonists based on uptake of DiI-AcLDL (1,1'-dioctadecyl-3,3,3'3'-tetramethylindocarbocyanine perchlorate-labeled LDL) by the transfected HEK 293 cells. For most assays, HEK 293 cells transfected with SR-AI were used, although both SR-AI and SR-AII appear to have equivalent activity. Briefly, HEK 293 cells were seeded at $2\times10^4$ cells/well in a 96-well plate in EMEM with 2 mM glutamine, 10% FBS, and 0.4 mg/mL geneticin. The cells showed essentially 100% attachment and achieved confluency by 3 days. Testing was performed in serum-free EMEM containing 2 mg/mL BSA. Confluent cells were incubated with DiI-AcLDL (final concentration, 2 $\mu$g/mL) in the absence or presence of the tested SR-A antagonists (quadruplicate determinations) for 4 h at 37° C. During aspiration of solutions and a Loche's buffer wash, there was a minimal detachment of cells because of their enhanced attachment relative to unmodified 293 cells. Results were quantified with a CytoFluro 2350 fluorescence plate reader at 530 nm excitation/590 nm emission. Background fluorescence of unlabeled cells was substracted from DiI-AcLDL fluorescence values (quadraplicate determinations), and results were expressed as percent total DiI fluorescence of cells incubated in the absence of SR-A antagonists.

Radioligand Assay

This assay was used to determine the effectiveness of an SR-A antagonist in blockage of SR-A degradation and binding/internalization of [$^{125}$I]AcLDL, and was adopted from previous studies (Goldstein et al. *Proc. Natl. Sci. USA* 1979, 76, 333–337; Goldstein et al. *Methods Enzymol.* 1983, 98, 181–190; Lysko et al. *J. Pharmacol. Exp. Ther.* 1999, 289, 1277–1285; PCT patent applications WO 99/07382, WO 00/06147, and WO 00/03704). Briefly, HEK 293 cells transfected with SR-AI or SR-AII were seeded at $2\times10^5$ cells/mL/well in a 24-well dish in EMEM supplemented with 2 mM glutamine, 10% FBS, and 0.4 mg/mL geneticin. After 2–3 days, medium was replaced with 500 $\mu$L of serum-free medium containing 2 mg/mL BSA and [$^{125}$I] AcLDL (iodinated actylated low density lipoprotein) at 5 $\mu$g/mL, and cells The cells showed essentially 100% attachment and achieved confluency by 3 days. Testing was performed in serum-free EMEM containing 2 mg/mL BSA, and cells were incubated at 37° C. for 5 h. After this suitable period for ligand degradation, cells were removed to 4° C. room. Supernatant was removed into trichloroacetic acid, and the mixture was centrifuged. The supernatant was chloroform extracted to isolate [$^{125}$I]monoiodotyrosine, the degradation product of [$^{125}$I]ACLDL, and portions were counted to determine the degradative activity. Blank plastic wells containing equivalent amounts of ligand without cells were incubated and processed in the same fashion to determine background ligand degradation, which was substracted from the total counts. Nonspecific binding was determined by incubation with poly I at 100 $\mu$g/mL. To determine cell-associated ligand, cell monolayers were washed and incubated at 4° C. with ice-cold buffer A containing 150 mM NaCl, 50 mM Tris-HCl, and 2 mg/mL BSA, pH 7.4, to eliminate nonspecifically bound counts. Cells were washed three times rapidly with 1 mL, incubated twice for 10 min each in 1 mL of buffer A without BSA. After aspiration of all wash buffer, cells were lysed in 0.1 N NaOH and removed to counting vials for determination of binding/uptake and sequential protein determination (Piece BCA assay). The present active yield $IC_{50}$ values of <50 $\mu$M in degradation assays and <100 mM in binding/uptake assays. In general, triplicate determinations were made for each data point within an experiment, and n equals the number of experiments performed.

Rabbits Model for Imaging Experimental Atherosclerosis

The study involves the use of male New Zealand white rabbits, 3–4 kg, fed with either normal rabbit diet as controls or a diet with 1.5% cholesterol added (Bio-Serv, Inc., Frechtown, N.J.) for 3 months. After 1 week of the hyperlipidemic diet, the abdominal aorta was denuded of endothelium by a modified Baumgartener technique (Baumgartener, H. R. *Z. Gesamte Exp. Med.* 1963, 137, 227–249; Narula et al. *Circulation* 1995, 92, 474–484; Narula et al. *J. Nucl. Cardiol.* 1996, 3, 231–241; Elmaleh et al. *Proc. Natl. Sci. USA* 1998, 95, 691–695). Briefly, each animal was anethetized with a mixture of ketamine and xylazine (100 mg/mL, 10:1 v:/v; 1.5–2.5 mL/sc), and the right femoral artery was isolated. A 4F Fogarty embolectomy catheter was introduced through an arteriotomy and advanced under fluoroscopic guidance to the level of the diaphragm. The catheter was inflated to a pressure of 3 psi above the balloon inflation pressure with radiographic contrast media (Conray, Mallinckrodt), and three passes were made down the abdominal aorta with the inflated catheter. The femoral artery was then ligated, and the wound was closed. The animals were allowed to recover from anesthesia and then returned to their cages. The animals continued to consume a hyperlipidemic diet for 11 additional weeks.

After 3 month on the hyperlipidemic diet, animals for imaging studies were injected into the marginal ear vein with approximately 0.5 mCi of the radiopharmaceutical. The animals are positioned on the camera head so as to image the anterior or posterior of the animals. Serial 5 minute dynamic images are acquired over 2 hours using a 256×256 matrix and a zoom of 2×. A known source is placed in the image field (20–90 μCi) to evaluate region of interest (ROI) uptake. Images were also acquired 24 hours post injection to determine retention of the compound in the aorta. Upon completion of the study, the images are evaluated by manually circumscribing the aorta region as the target region of interest (ROI) and a background site in the surrounding area. The uptake is determined by taking the fraction of the total counts in an inscribed area for ROI/source and multiplying the known μCi. After imaging, the animals were scarified for biodistribution or autoradiographic examinations of the appropriate organs.

This model can also be used to assess the effectiveness of radiopharmaceuticals of the present invention comprised of a positron-emitting isotope. The radiopharmaceuticals are administered in appropriate amounts and the uptake in the aorta can be quantified either non-invasively by PET imaging or by excision of the aorta and counting the amount of radioactivity present by standard techniques.

This model can also be used to assess the compounds of the present invention comprised of paramagnetic metals as MRI contrast agents. After administration of the appropriate amount of the paramagnetic compounds, the whole animal can be placed in a commercially available magnetic resonance imager to image the aorta. The effectiveness of the contrast agents can be readily seen by comparison to the images obtain from animals that are not administered a contrast agent.

This model can also be used to assess the compounds of the present invention comprised of heavy atoms as X-ray contrast agents. After administration of the appropriate amount of the X-ray absorbing compounds, the whole animal can be placed in a commercially available X-ray imager to image the aorta. The effectiveness of the contrast agents can be readily seen by comparison to the images obtain from animals that are not administered a contrast agent.

This model can also be used to assess the compounds of the present invention comprised of an echogenic gas containing surfactant microsphere as ultrasound contrast agents. After administration of the appropriate amount of the echogenic compounds, the tumors in the animal can be imaging using an ultrasound probe held proximate to the aorta. The effectiveness of the contrast agents can be readily seen by comparison to the images obtain from animals that are not administered a contrast agent.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula (I):

wherein

M is a radionuclide selected from: $^{99m}Tc$, $^{117m}Sn$, $^{111}In$, $^{97}Ru$, $^{67}Ga$, $^{68}Ga$, $^{89}Zr$, $^{177}Lu$, $^{47}Sc$, $^{105}Rh$, $^{188}Re$, $^{60}Cu$, $^{62}Cu$, $^{64}Cu$ and $^{67}Cu$, or a paramagnetic metal ion of atomic number 21–29, 42–44, or 58–70, or a heavy metal ion of atomic number 21–31, 39–49, 50, 56–80, 82, 83, 90;

$C_h$ is a metal chelator having a formula selected from the group:

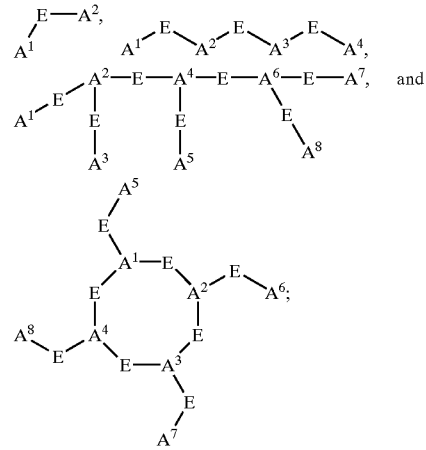

wherein $A^1$, $A^2$, $A^3$, $A^4$, $A^5$, $A^6$, $A^7$, and $A^8$ are independently selected at each occurrence from the group: $NR^{19}$, $NR^{19}R^{20}$, S, SH, O, OH, $PR^{19}$, $PR^{19}R^{20}$, $P(O)R^{21}R^{22}$, and a direct bond to $L_n$;

E is a direct bond, CH, or a spacer group independently selected at each occurrence from the group: $(C_1-C_{10})$ alkyl substituted with 0–3 $R^{23}$, aryl substituted with 0–3 $R^{23}$, $(C_3-C_{10})$cycloalkyl substituted with 0–3 $R^{23}$, heterocyclo-$(C_1-C_{10})$alkyl substituted with 0–3 $R^{23}$, wherein the heterocyclo group is a 5–10 membered heterocyclic ring system containing 1–4 heteroatoms independently selected from N, S, and O, $(C_6-C_{10})$aryl-$(C_1-C_{10})$alkyl substituted with 0–3 $R^{23}$, $(C_1-C_{10})$alkyl-$(C_6-C_{10})$aryl-substituted with 0–3 $R^{23}$, and a 5–10 membered heterocyclic ring system containing 1–4 heteroatoms independently selected from N, S, and O and substituted with 0–3 $R^{23}$;

$R^{19}$ and $R^{20}$ are each independently selected from the group: a direct bond to $L_n$, hydrogen, $(C_1-C_{10})$alkyl substituted with 0–3 $R^{23}$, aryl substituted with 0–3 $R^{23}$, $(C_3-C_{10})$cycloalkyl substituted with 0–3 $R^{23}$, heterocyclo-$(C_1-C_{10})$alkyl substituted with 0–3 $R^{23}$, wherein the heterocyclo group is a 5–10 membered heterocyclic ring system containing 1–4 heteroatoms independently selected from N, S, and O, $(C_6-C_{10})$aryl-$(C_1-C_{10})$alkyl substituted with 0–3 $R^{23}$, $(C_1-C_{10})$alkyl-$(C_6-C_{10})$aryl-substituted with 0–3 $R^{23}$, a 5–10 membered heterocyclic ring system containing 1–4 heteroatoms independently selected from N, S, and O and substituted with 0–3 $R^{23}$, and an electron, provided that when one of $R^{19}$ or $R^{20}$ is an electron, then the other is also an electron;

$R^{21}$ and $R^{22}$ are each independently selected from the group: a direct bond to $L_n$, —OH, $(C_1-C_{10})$alkyl substituted with 0–3 $R^{23}$, $(C_1-C_{10})$alkyl substituted with 0–3 $R^{23}$, aryl substituted with 0–3 $R^{23}$, $(C_3-C_{10})$ cycloalkyl substituted with 0–3 $R^{23}$, heterocyclo-$(C_1-C_{10})$alkyl substituted with 0–3 $R^{23}$, wherein the heterocyclo group is a 5–10 membered heterocyclic ring system containing 1–4 heteroatoms independently selected from N, S, and O, $(C_6-C_{10})$aryl-$(C_1-C_{10})$alkyl substituted with 0–3 $R^{23}$, $(C_1-C_{10})$alkyl-$(C_6-C_{10})$aryl-substituted with 0–3 $R^{23}$, and a 5–10 membered heterocyclic ring system containing 1–4 heteroatoms independently selected from N, S, and O and substituted with 0–3 $R^{23}$;

$R^{23}$ is independently selected at each occurrence from the group: a direct bond to $L_n$, =O, F, Cl, Br, I, —$CF_3$, —CN, —$CO_2R^{24}$, —C(=O)$R^{24}$, —C(=O)N($R^{24}$)$_2$, —CHO, —$CH_2OR^{24}$, —OC(=O)$R^{24}$, —OC(=O)O$R^{24a}$, —O$R^{24}$, —OC(=O)N($R^{24}$)$_2$, —$NR^{25}$C(=O)$R^{24}$, —$NR^{25}$C(=O)O$R^{24a}$, —$NR^{25}$C(=O)N($R^{24}$)$_2$, —$NR^{25}SO_2$N($R^{24}$)$_2$, —$NR^{25}SO_2R^{24a}$, —$SO_3H$, —$SO_2R^{24a}$, —$SR^{24}$, —S(=O)$R^{24a}$, $SO_2$N($R^{24}$)$_2$, —N($R^{24}$)$_2$, —NHC(=S)NH$R^{24}$, =NO$R^{24}$, $NO_2$, —C(=O)NHO$R^{24}$, —C(=O)NHN$R^{24}R^{24a}$, —$OCH_2CO_2H$, 2-(1-morpholino)ethoxy, ($C_1$–$C_5$) alkyl, ($C_2$–$C_4$)alkenyl, ($C_3$–$C_6$)cycloalkyl, ($C_3$–$C_6$) cycloalkylmethyl, ($C_2$–$C_6$)alkoxyalkyl, aryl substituted with 0–2 $R^{24}$, and a 5–10 membered heterocyclic ring system containing 1–4 heteroatoms independently selected from N, S, and O;

$R^{24}$, $R^{24a}$, and $R^{25}$ are independently selected at each occurrence from the group: a direct bond to $L_n$, H, ($C_1$–$C_6$)alkyl, phenyl, benzyl, ($C_1$–$C_6$)alkoxy, halide, nitro, cyano, and trifluoromethyl;

$L_n$ is a linking group having the formula:

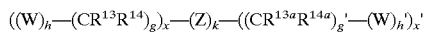

wherein,

W is independently selected at each occurrence from the group: O, S, NH, NHC(=O), C(=O)NH, $NR^{15}$C(=O), C(=O)$NR^{15}$, C(=O), C(=O)O, OC(=O), NHC(=S)NH, NHC(=O)NH, $SO_2$, $SO_2$NH, ($OCH_2CH_2$)$_s$, ($CH_2CH_2O$)$_s'$, ($OCH_2CH_2CH_2$)$_{s''}$, ($CH_2CH_2CH_2O$)$_t$, and (aa)$_{t'}$;

aa is independently at each occurrence an amino acid;

Z is selected from the group: aryl substituted with 0–3 $R^{16}$, ($C_3$–$C_{10}$)cycloalkyl substituted with 0–3 $R^{16}$, and a 5–10 membered heterocyclic ring system containing 1–4 heteroatoms independently selected from N, S, and O and substituted with 0–3 $R^{16}$;

$R^{13}$, $R^{13a}$, $R^{14}$, $R^{14a}$, and $R^{15}$ are independently selected at each occurrence from the group: H, =O, COOH, $SO_3H$, $PO_3H$, ($C_1$–$C_5$)alkyl substituted with 0–3 $R^{16}$, aryl substituted with 0–3 $R^{16}$, benzyl substituted with 0–3 $R^{16}$, and ($C_1$–$C_5$)alkoxy substituted with 0–3 $R^{16}$, NHC(=O)$R^{17}$, C(=O)NH$R^{17}$, NHC(=O)NH$R^{17}$, NH$R^{17}$, $R^{17}$, and a direct bond to $C_h$;

$R^{16}$ is independently selected at each occurrence from the group: a direct bond to $C_h$, COO$R^{17}$, C(=O)NH$R^{17}$, NHC(=O)$R^{17}$, OH, NH$R^{17}$, $SO_3H$, $PO_3H$, —$OPO_3H_2$, —$OSO_3H$, aryl substituted with 0–3 $R^{17}$, ($C_1$–$C_5$)alkyl substituted with 0–1 $R^{18}$, ($C_1$–$C_5$)alkoxy substituted with 0–1 $R^{18}$, and a 5–10 membered heterocyclic ring system containing 1–4 heteroatoms independently selected from N, S, and O and substituted with 0–3 $R^{17}$;

$R^{17}$ is independently selected at each occurrence from the group: H, alkyl substituted with 0–1 $R^{18}$, aryl substituted with 0–1 $R^{18}$, a 5–10 membered heterocyclic ring system containing 1–4 hetero atoms independently selected from N, S, and O and substituted with 0–1 $R^{18}$, ($C_3$–$C_{10}$)cycloalkyl substituted with 0–1 $R^{18}$, polyalkylene glycol substituted with 0–1 $R^{18}$, carbohydrate substituted with 0–1 $R^{18}$, cyclodextrin substituted with 0–1 $R^{18}$, amino acid substituted with 0–1 $R^{18}$, polycarboxyalkyl substituted with 0–1 $R^{18}$, polyazaalkyl substituted with 0–1 $R^{18}$, peptide substituted with 0–1 $R^{18}$, wherein the peptide is comprised of 2–10 amino acids, 3,6-O-disulfo-B-D-galactopyranosyl, bis(phosphonomethyl)glycine, and a direct bond to $C_h$;

$R^{18}$ is a direct bond to $C_h$;

k is selected from 0, 1, and 2;

h is selected from 0, 1, and 2;

h' is selected from 0, 1, and 2;

g is selected from 0, 1, 2, 3, 4, 5, 6, 7, 8, 9, and 10;

g' is selected from 0, 1, 2, 3, 4, 5, 6, 7, 8, 9, and 10;

s is selected from 0, 1, 2, 3, 4, 5, 6, 7, 8, 9, and 10;

s' is selected from 0, 1, 2, 3, 4, 5, 6, 7, 8, 9, and 10;

s'' is selected from 0, 1, 2, 3, 4, 5, 6, 7, 8, 9, and 10;

t is selected from 0, 1, 2, 3, 4, 5, 6, 7, 8, 9, and 10;

t' is selected from 0, 1, 2, 3, 4, 5, 6, 7, 8, 9, and 10;

x is selected from 0, 1, 2, 3, 4, and 5;

x' is selected from 0, 1, 2, 3, 4, and 5;

n is an integer from 1 to 10;

wherein $L_n$ is not a direct bond if $C_h$ is a direct bond;

BM is an SR-A antagonist of formula:

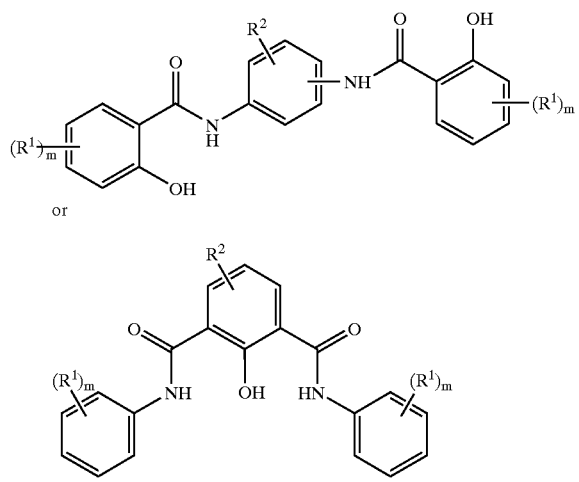

wherein $R^1$ is independently selected from: H, $R^1$-benzamido, $R^1$-benzylether, $R^1$-benzylamino, amino, fluoralkyl, halo, cyano, nitro, aryloxyl, haloaryl, aryl, alkoxy, and 1,2-benzo; or $R^1$ represents a fused ring forming naphthalene moiety with the six membered aryl ring it substitutes;

$R^2$ is a direct bond to Ln; and m is an integer from 1 to 4;

or a pharmaceutically acceptable salt thereof.

2. The compound of claim 1 wherein $C_h$ is

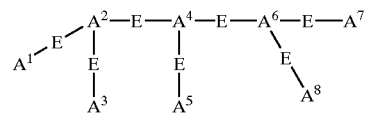

wherein, $A^1$ is selected from the group: OH, and a direct bond to $L_n$;

$A^2$, $A^4$, and $A^6$ are each N;

$A^3$, $A^5$, and $A^8$ are each OH;

$A^7$ is a direct bond to $L_n$ or NH-bond to $L_n$;

E is a $C_2$ alkyl substituted with 0–1 $R^{23}$; and $R^{23}$ is =O.

3. The compound of claim 1 wherein $C_h$ is

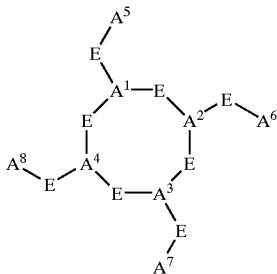

wherein, $A^1$ is selected from the group: OH, and a direct bond to $L_n$;

$A^2$, $A^3$ and $A^4$ are each N;

$A^5$, $A^6$ and $A^8$ are each OH;

$A^7$ is a direct bond to $L_n$;

E is a $C_2$ alkyl substituted with 0–1 $R^{23}$; and $R^{23}$ is =O.

4. The compound of claim 1 wherein $C_h$ is

wherein $A^1$ is $NH_2$;

E is a direct bond;

$A^2$ is $NHR^{19}$;

$R^{19}$ is a heterocycle substituted with $R^{23}$, the heterocycle being selected from pyridine and pyrimidine;

$R^{23}$ is selected from a direct bond to $L_n$, C(=O)NHR$^{24}$ and C(=O)R$^{24}$;

$R^{24}$ is a direct bond to $L_n$;

$R^{30}$ is selected from the group: —CO$_2$R$^{31}$, —OR$^{31}$, —SO$_3$H, and —N(R$^{31}$)$_2$; and $R^{31}$ is independently selected at each occurrence from the group: hydrogen and methyl.

5. The compound of claim 1 wherein $C_h$ is selected from the group: DTPA, DOTA, TETA, TRITA, HETA, DOTA-NHS, TETA-NHS, DOTA(Gly)3-L-(p-isothiocyanoto)-Phe-amide, and DO3A.

6. A compound of formula (I):

wherein,

M is radionuclide selected from: $^{99m}$Tc, $^{117m}$Sn, $^{111}$In, $^{97}$Ru, $^{67}$Ga, $^{68}$Ga, $^{89}$Zr, $^{177}$Lu, $^{47}$Sc, $^{105}$Rh; $^{188}$Re, $^{60}$Cu, $^{62}$Cu, $^{64}$Cu and $^{67}$Cu, or a paramagnetic metal ion of atomic number 21–29, 42–44, or 58–70, or a heavy metal ion of atomic number 21–31, 39–49, 50, 56–80, 82, 83, 90;

$C_h$ is a metal chelator having a formula selected from the group:

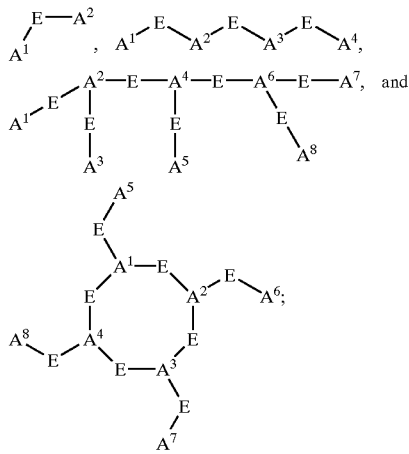

wherein, $A^1$, $A^2$, $A^3$, $A^4$, $A^5$, $A^6$, $A^7$, and $A^8$ are independently selected at each occurrence from the group: NR$^{19}$, NR$^{19}$R$^{20}$, S, SH, O, OH, PR$^{19}$, PR$^{19}$R$^{20}$, P(O)R$^{21}$R$^{22}$, and a direct bond to $L_n$;

E is a direct bond, CH, or a spacer group independently selected at each occurrence from the group: (C$_1$–C$_{10}$) alkyl substituted with 0–3 R$^{23}$, aryl substituted with 0–3 R$^{23}$, (C$_3$–C$_{10}$)cycloalkyl substituted with 0–3 R$^{23}$, heterocyclo-(C$_1$–C$_{10}$)alkyl substituted with 0–3 R$^{23}$, wherein the heterocyclo group is a 5–10 membered heterocyclic ring system containing 1–4 heteroatoms independently selected from N, S, and O, (C$_6$–C$_{10}$)aryl-(C$_1$–C$_{10}$)alkyl substituted with 0–3 R$^{23}$, (C$_1$–C$_{10}$)alkyl-(C$_6$–C$_{10}$)aryl-substituted with 0–3 R$^{23}$, and a 5–10 membered heterocyclic ring system containing 1–4 heteroatoms independently selected from N, S, and O and substituted with 0–3 R$^{23}$;

$R^{19}$ and $R^{20}$ are each independently selected from the group: a direct bond to $L_n$, hydrogen, (C$_1$–C$_{10}$)alkyl substituted with 0–3 R$^{23}$, aryl substituted with 0–3 R$^{23}$, (C$_1$–C$_{10}$)cycloalkyl substituted with 0–3 R$^{23}$, heterocyclo-(C$_1$–C$_{10}$)alkyl substituted with 0–3 R$^{23}$, wherein the heterocyclo group is a 5–10 membered heterocyclic ring system containing 1–4 heteroatoms independently selected from N, S, and O, (C$_6$–C$_{10}$)aryl-(C$_1$–C$_{10}$)alkyl substituted with 0–3 R$^{23}$, (C$_1$–C$_{10}$)alkyl-(C$_6$–C$_{10}$)aryl-substituted with 0–3 R$^{23}$, a 5–10 membered heterocyclic ring system containing 1–4 heteroatoms independently selected from N, S, and O and substituted with 0–3 R$^{23}$, and an electron, provided that when one of R$^{19}$ or R$^{20}$ is an electron, then the other is also an electron;

$R^{21}$ and $R^{22}$ are each independently selected from the group: a direct bond to $L_n$, —OH, (C$_1$–C$_{10}$)alkyl substituted with 0–3 R$^{23}$, (C$_1$–C$_{10}$)alkyl substituted with 0–3 R$^{23}$, aryl substituted with 0–3 R$^{23}$, (C$_3$–C$_{10}$) cycloalkyl substituted with 0–3 R$^{23}$, heterocyclo-(C$_1$–C$_{10}$)alkyl substituted with 0–3 R$^{23}$, wherein the heterocyclo group is a 5–10 membered heterocyclic ring system containing 1–4 heteroatoms independently selected from N, S, and O, (C$_6$–C$_{10}$)aryl-(C$_1$–C$_{10}$)alkyl substituted with 0–3 R$^{23}$, (C$_1$–C$_{10}$)alkyl-(C$_6$–C$_{10}$)aryl-substituted with 0–3 R$^{23}$, and a 5–10 membered heterocyclic ring system containing 1–4 heteroatoms independently selected from N, S, and O and substituted with 0–3 $R^{23}$;

$R^{23}$ is independently selected at each occurrence from the group: a direct bond to $L_n$, =O, F, Cl, Br, I, —$CF_3$, —CN, —$CO_2R^{24}$, —C(=O)$R^{24}$, —C(=O)N$(R^{24})_2$, —CHO, —$CH_2OR^{24}$, —OC(=O)$R^{24}$, —OC(=O)O$R^{24a}$, —O$R^{24}$, —OC(=O)N$(R^{24})_2$, —$NR^{25}$C(=O)$R^{24}$, —$NR^{25}$C(=O)O$R^{24a}$, —$NR^{25}$C(=O)N$(R^{24})_2$, —$NR^{25}SO_2$N$(R^{24})_2$, —$NR^{25}SO_2R^{24a}$, —$SO_3H$, —$SO_2R^{24a}$, —$SR^{24}$, —S(=O)$R^{24a}$, —$SO_2$N$(R^{24})_2$, —N$(R^{24})_2$, —NHC(=S)NH$R^{24}$, =NO$R^{24}$, $NO_2$, —C(=O)NHO$R^{24}$, —C(=O)NHN$R^{24}R^{24a}$, —$OCH_2CO_2H$, 2-(1-morpholino)ethoxy, ($C_1$–$C_5$) alkyl, ($C_2$–$C_4$)alkenyl, ($C_3$–$C_6$)cycloalkyl, ($C_3$–$C_6$) cycloalkylmethyl, ($C_2$–$C_6$)alkoxyalkyl, aryl substituted with 0–2 $R^{24}$, and a 5–10 membered heterocyclic ring system containing 1–4 heteroatoms independently selected from N, S, and O;

$R^{24}$, $R^{24a}$, and $R^{25}$ are independently selected at each occurrence from the group: a direct bond to $L_n$, H, ($C_1$–$C_{10}$)alkyl, phenyl, benzyl, ($C_1$–$C_{10}$)alkoxy, halide, nitro, cyano, and trifluoromethyl;

$L_n$ is a linking group having the formula:

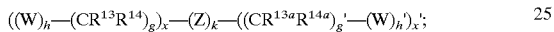

wherein,

W is independently selected at each occurrence from the group: O, S, Nil, NHC(=O), C(=O)NH, $NR^{15}$C(=O), C(=O)$NR^{15}$, C(=O), C(=O)O, OC(=O), NHC(=S)NH, NHC(=O)NH, $SO_2$, $SO_2$NH, $(OCH_2CH_2)_s$, $(CH_2CH_2O)_{s'}$, $(OCH_2CH_2CH_2)_{s''}$, $(CH_2CH_2CH_2O)_t$, and $(aa)_{t'}$;

aa is independently at each occurrence an amino acid;

Z is selected from the group: aryl substituted with 0–3 $R^{16}$, ($C_3$–$C_{10}$)cycloalkyl substituted with 0–3 $R^{16}$, and a 5–10 membered heterocyclic ring system containing 1–4 heteroatoms independently selected from N, S, and O and substituted with 0–3 $R^{16}$;

$R^{13}$, $R^{13a}$, $R^{14}$, $R^{14a}$, and $R^{15}$ are independently selected at each occurrence from the group: H, =O, COOH, $SO_3H$, $PO_3H$, ($C_1$–$C_5$)alkyl substituted with 0–3 $R^{16}$, aryl substituted with 0–3 $R^{16}$, benzyl substituted with 0–3 $R^{16}$, and ($C_1$–$C_5$)alkoxy substituted with 0–3 $R^{16}$, NHC(=O)$R^{17}$, C(=O)NH$R^{17}$, NHC(=O)NH$R^{17}$, NH$R^{17}$, $R^{17}$, and a direct bond to $C_h$;

$R^{16}$ is independently selected at each occurrence from the group: a direct bond to $C_h$, COO$R^{17}$, C(=O)NH$R^{17}$, NHC(=O)$R^{17}$, OH, NH$R^{17}$, $SO_3H$, $PO_3H$, —$OPO_3H_2$, —$OSO_3H$, aryl substituted with 0–3 $R^{17}$, ($C_1$–$C_5$)alkyl substituted with 0–1 $R^{18}$, ($C_1$–$C_5$)alkoxy substituted with 0–1 $R^{18}$, and a 5–10 membered heterocyclic ring system containing 1–4 heteroatoms independently selected from N, S, and O and substituted with 0–3 $R^{17}$;

$R^{17}$ is independently selected at each occurrence from the group: H, alkyl substituted with 0–1 $R^{18}$, aryl substituted with 0–1 $R^{18}$, a 5–10 membered heterocyclic ring system containing 1–4 hetero atoms independently selected from N, S, and O and substituted with 0–1 $R^{18}$, ($C_3$–$C_{10}$)cycloalkyl substituted with 0–1 $R^{18}$, polyalkylene glycol substituted with 0–1 $R^{18}$, carbohydrate substituted with 0–1 $R^{18}$, cyclodextrin substituted with 0–1 $R^{18}$, amino acid substituted with 0–1 $R^{18}$, polycarboxyalkyl substituted with 0–1 $R^{18}$, polyazaalkyl substituted with 0–1 $R^{18}$, peptide substituted with 0–1 $R^{18}$, wherein the peptide is comprised of 2–10 amino acids, 3,6-O-disulfo-B-D-galactopyranosyl, bis(phosphonomethyl)glycine, and a direct bond to $C_h$;

$R^{18}$ is a direct bond to $C_h$;

k is selected from 0, 1, and 2;

h is selected from 0, 1, and 2;

h' is selected from 0, 1, and 2;

g is selected from 0, 1, 2, 3, 4, 5, 6, 7, 8, 9, and 10;

g' is selected from 0, 1, 2, 3, 4, 5, 6, 7, 8, 9, and 10;

s is selected from 0, 1, 2, 3,4, 5, 6, 7, 8, 9, and 10;

s' is selected from 0, 1, 2, 3, 4, 5, 6, 7, 8, 9, and 10;

s" is selected from 0, 1, 2, 3, 4, 5, 6, 7, 8, 9, and 10;

t is selected from 0, 1, 2, 3, 4, 5, 6, 7, 8, 9, and 10;

t' is selected from 0, 1, 2, 3, 4, 5, 6, 7, 8, 9, and 10;

x is selected from 0, 1, 2, 3, 4, and 5;

x' is selected from 0, 1, 2, 3, 4, and 5;

n is an integer from 1 to 10;

wherein $L_n$ is not a direct bond if $C_h$ is a direct bond;

BM is an SR-A antagonist of formula:

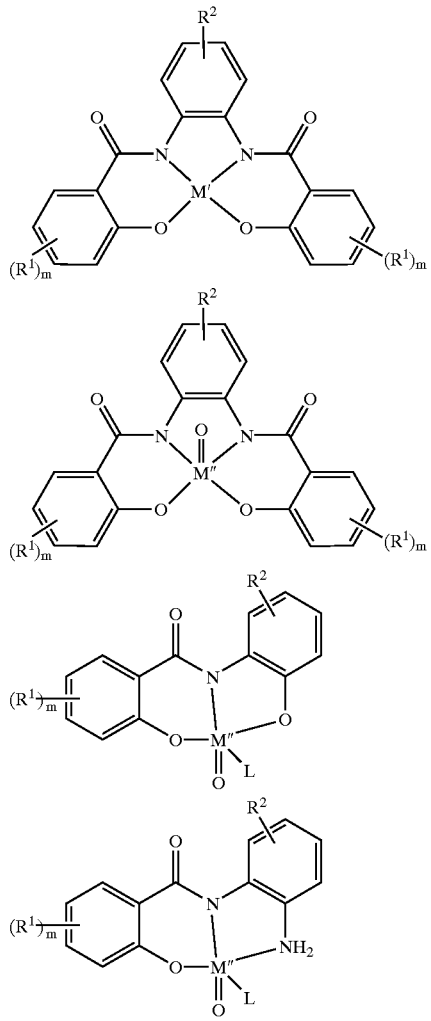

wherein $R^1$ is independently selected from: H, $R^1$-benzamido, $R^1$-benzylether, $R^1$-benzylamino, amino, fluoralkyl, halo, cyano, nitro, aryloxyl, haloaryl, aryl, alkoxy, and 1,2-benzo; or $R^1$ represents a fused ring forming naphthalene moiety with the six membered aryl ring it substitutes;

$R^2$ is a direct bond to Ln;

m is an integer from 1 to 4;

M' is a metal ion selected from Fe(III), Os(III), Co(III), Ni(II), or Cu(II);

M" is a metal-containing moiety selected from: V=O, Mo=O, or Re=O; and

L is a coligand selected from: trialkylphosphine, triarylphosphine, triarylyalkylphosphine, pyridine or pyridine analog with appropriate substituent on the pyridine ring;

or a pharmaceutically acceptable salt thereof.

7. The compound of claim 6 wherein $C_h$ is

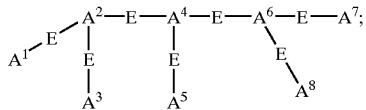

wherein, $A^1$ is selected from the group: OH, and a direct bond to $L_n$;

$A^2$, $A^4$, and $A^6$ are each N;

$A^3$, $A^5$, and $A^8$ are each OH;

$A^7$ is a direct bond to $L_n$ or NH-bond to $L_n$;

E is a $C_2$ alkyl substituted with 0–1 $R^{23}$; and $R^{23}$ is =O.

8. The compound of claim 6 wherein $C_h$ is

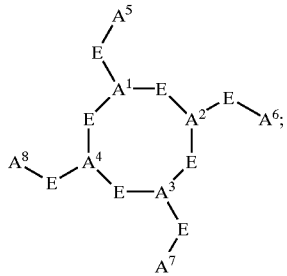

wherein, $A^1$ is selected from the group: OH, and a direct bond to $L_n$;

$A^2$, $A^3$ and $A^4$ are each N;

$A^5$, $A^6$ and $A^8$ are each OH;

$A^7$ is a direct bond to $L_n$;

E is a $C_2$ alkyl substituted with 0–1 $R^{23}$; and $R^{23}$ is =O.

9. The compound of claim 6 wherein $C_h$ is

wherein, $A^1$ is $NH_2$;

E is a direct bond;

$A^2$ is $NHR^{19}$;

$R^{19}$ is a heterocycle substituted with $R^{23}$, the heterocycle being selected from pyridine and pyrimidine;

$R^{23}$ is selected from a direct bond to $L_n$, C(=O)$NHR^{24}$ and C(=O)$R^{24}$;

$R^{24}$ is a direct bond to $L_n$;

$R^{30}$ is selected from the group: —$CO_2R^{31}$, —$OR^{31}$, —$SO_3H$, and —$N(R^{31})_2$; and $R^{31}$ is independently selected at each occurrence from the group: hydrogen and methyl.

10. The compound of claim 6 wherein $C_h$ is selected from the group: DTPA, DOTA, TETA, TRITA, HETA, DOTA-NHS, TETA-NHS, DOTA(Gly)3-L-(p-isothiocyanoto)-Phe-amide, and DO3A.

11. A compound of the formula:

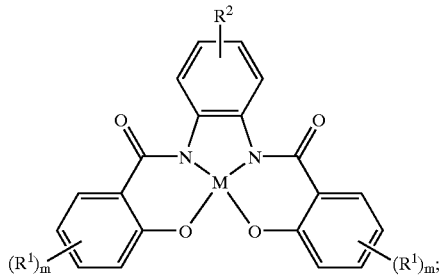

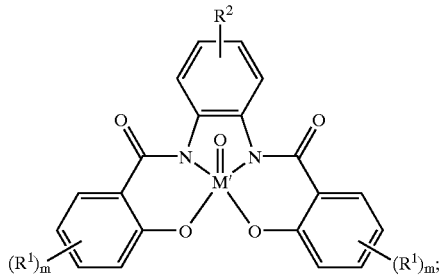

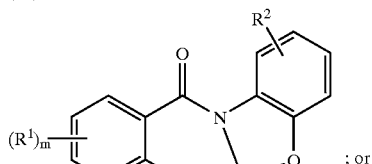

; or

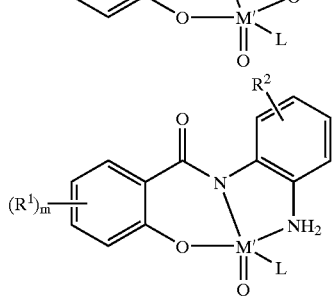

wherein

M is radionuclide selected from: $^{60}$Cu, $^{62}$Cu, $^{64}$Cu and $^{67}$Cu;

M' is $^{99m}$Tc or $^{188}$Re;

$R^1$ is independently selected from: H, $R^1$-benzamido, $R^1$-benzylether, $R^1$-benzylamino, amino, fluoralkyl, halo, cyano, nitro, aryloxyl, haloaryl, aryl, alkoxy, and 1,2-benzo; or $R^1$ represents a fused ring forming naphthalene moiety with the six membered aryl ring it substitutes;

$R^2$ is independently selected from: H, fluoralkyl, halo, aryloxyl, haloaryl, aryl, alkoxy, and 1,2-benzo; or $R^2$ represents a fused ring forming naphthalene moiety with the six membered aryl ring it substitutes;

m is an integer from 1 to 4; and

L is a coligand selected from: trialkylphosphine, triarylphosphine, triarylyalkylphosphine, pyridine or pyridine analog;

or a pharmaceutically acceptable salt thereof.

12. A method to diagnose a cardiovascular disease in a patient comprising administering to the patient in need of such diagnosis an effective amount of a compound of claim 1 and detecting the presence of the compound.

13. The method of claim 12 wherein the cardiovascular disease is selected from:

atherosclerosis, vulnerable plaque, coronary artery disease, renal disease, thrombosis, transient ischemia due to clotting, stroke, myocardial infarction, organ transplant, organ failure and hypercholesterolemia.

14. A method to monitor a cardiovascular disease in a patient comprising administering to the patient in need of such monitoring an effective amount of a compound of claim 1 and detecting the presence of the compound.

15. The method of claim 14 wherein the cardiovascular disease is selected from:

atherosclerosis, vulnerable plaque, coronary artery disease, renal disease, thrombosis, transient ischemia due to clotting, stroke, myocardial infarction, organ transplant, organ failure and hypercholesterolemia.

16. A method to monitor the progression of an atherosclerotic lesion in a patient comprising administering to the patient in need of such monitoring an effective amount of a compound of claim 1 and detecting the presence of the compound.

17. A method to detect vulnerable plaque comprising administering to the patient in need of such detection a compound of claim 1 and detecting the presence of the compound.

18. The method of claim 12 wherein the detection comprises magnetic resonance imaging.

19. The method of claim 12 wherein the detection comprises X-ray imaging.

20. A method to diagnose a cardiovascular disease in a patient comprising administering to the patient in need of such diagnosis an effective amount of a compound of claim 6 and detecting the presence of the compound.

21. The method of claim 20 wherein the cardiovascular disease is selected from:

atherosclerosis, vulnerable plaque, coronary artery disease, renal disease, thrombosis, transient ischemia due to clotting, stroke, myocardial infarction, organ transplant, organ failure and hypercholesterolemia.

22. A method to monitor a cardiovascular disease in a patient comprising administering to the patient in need of such monitoring an effective amount of a compound of claim 6 and detecting the presence of the compound.

23. The method of claim 22 wherein the cardiovascular disease is selected from:

atherosclerosis, vulnerable plaque, coronary artery disease, renal disease, thrombosis, transient ischemia due to clotting, stroke, myocardial infarction, organ transplant, organ failure and hypercholesterolemia.

24. A method to monitor the progression of an atherosclerotic lesion in a patient comprising administering to the patient in need of such monitoring an effective amount of a compound of claim 6 and detecting the presence of the compound.

25. A method to detect vulnerable plaque comprising administering to the patient in need of such detection a compound of claim 6 and detecting the presence of the compound.

26. The method of claim 20 wherein the detection comprises magnetic resonance imaging.

27. The method of claim 20 wherein the detection comprises X-ray imaging.

28. A method of radio-imaging in a patient comprising administering to a patient in need of such radio-imaging a compound of claim 11 and detecting the presence of the compound.

29. A pharmaceutical composition comprising a predetermined quantity of a compound of claim 1, or a pharmaceutically acceptable salt thereof; and a pharmaceutically acceptable carrier or diluent.

30. The pharmaceutical composition of claim 29 further comprising an effective amount of a stabilizer.

31. The pharmaceutical composition of claim 30 wherein the stabilizer is selected from the group:

ascorbic acid, benzyl alcohol, gentisic acid or a metal salt thereof, p-aminobenzoic acid or a salt thereof, cysteamine, 5-amino-2-hydroxybenzoic acid or a metal salt thereof, nicotinic acid or a metal salt thereof, nicotinamide, a polyhydroxylated aromatic compound, an aromatic amine, and a hydroxylated aromatic amine.

32. A pharmaceutical composition comprising a predetermined quantity of a compound of claim 6, or a pharmaceutically acceptable salt thereof; and a pharmaceutically acceptable carrier or diluent.

33. The pharmaceutical composition of claim 32 further comprising an effective amount of a stabilizer.

34. The pharmaceutical composition of claim 33 wherein the stabilizer is selected from the group:

ascorbic acid, benzyl alcohol, gentisic acid or a metal salt thereof, p-aminobenzoic acid or a salt thereof, cysteamine, 5-amino-2-hydroxybenzoic acid or a metal salt thereof, nicotinic acid or a metal salt thereof, nicotinamide, a polyhydroxylated aromatic compound, an aromatic amine, and a hydroxylated aromatic amine.

35. A pharmaceutical composition comprising a predetermined quantity of a compound of claim 11, or a pharmaceutically acceptable salt thereof; and a pharmaceutically acceptable carrier or diluent.

36. The pharmaceutical composition of claim 35 further comprising an effective amount of a stabilizer.

37. The pharmaceutical composition of claim 36 wherein the stabilizer is selected from the group:

ascorbic acid, benzyl alcohol, gentisic acid or a metal salt thereof, p-aminobenzoic acid or a salt thereof, cysteamine, 5-amino-2-hydroxybenzoic acid or a metal salt thereof, nicotinic acid or a metal salt thereof, nicotinamide, a polyhydroxylated aromatic compound, an aromatic amine, and a hydroxylated aromatic amine.

38. A kit comprising a sealed vial comprising a predetermined quantity of a compound of claim 1 or a pharmaceutically acceptable salt thereof; and a pharmaceutically acceptable carrier or diluent.

39. The kit of claim 38 further comprising at least one of a reducing agent, a lyophilization aid, and a weak transfer ligand.

40. A kit comprising a sealed vial comprising a predetermined quantity of a compound of claim 6 or a pharmaceutically acceptable salt thereof; and a pharmaceutically acceptable carrier or diluent.

41. The kit of claim 40 further comprising at least one of a reducing agent, a lyophilization aid, and a weak transfer ligand.

42. A kit comprising a sealed vial comprising a predetermined quantity of a compound of claim 11 or a pharmaceutically acceptable salt thereof; and a pharmaceutically acceptable carrier or diluent.

43. The kit of claim 42 further comprising at least one of a reducing agent, a lyophilization aid, and a weak transfer ligand.

44. A kit comprising (a) a first vial comprising a predetermined quantity of a compound of claim 1, or a pharmaceutically acceptable salt thereof; and (b) a second vial comprising a pharmaceutically acceptable carrier or diluent.

45. The kit of claim 44 further comprising at least one of a reducing agent, a lyophilization aid, and a weak transfer ligand.

46. A kit comprising (a) a first vial comprising a predetermined quantity of a compound of claim 6, or a pharmaceutically acceptable salt thereof; and (b) a second vial comprising a pharmaceutically acceptable carrier or diluent.

47. The kit of claim 46 further comprising at least one of a reducing agent, a lyophilization aid, and a weak transfer ligand.

48. A kit comprising (a) a first vial comprising a predetermined quantity of a compound of claim 11, or a pharmaceutically acceptable salt thereof; and (b) a second vial comprising a pharmaceutically acceptable carrier or diluent.

49. The kit of claim 48 further comprising at least one of a reducing agent, a lyophilization aid, and a weak transfer ligand.

* * * * *